United States Patent
Breiter et al.

(10) Patent No.: US 6,517,812 B1
(45) Date of Patent: Feb. 11, 2003

(54) INHIBITION OF PSYCHOSTIMULANT-INDUCED AND NICOTINE-INDUCED CRAVING

(75) Inventors: Hans C. Breiter, Lincoln, MA (US); Bruce R. Rosen, Lexington, MA (US); John J. A. Marota, Boston, MA (US); Joseph B. Mandeville, Somerville, MA (US); Barry E. Kosofsky, Swampscott, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/159,659

(22) Filed: Sep. 24, 1998

Related U.S. Application Data

(60) Provisional application No. 60/059,838, filed on Sep. 24, 1997.

(51) Int. Cl.[7] .......................... A61K 51/00; A61M 36/14

(52) U.S. Cl. ...................... 424/9.2; 424/1.11; 424/1.65; 424/9.1

(58) Field of Search ............................... 424/9.36, 1.11, 424/1.65, 9.1, 9.2, 9.3; 514/282

(56) References Cited

U.S. PATENT DOCUMENTS

| | | | |
|---|---|---|---|
| 4,935,429 A | 6/1990 | Dackis et al. ................ | 514/288 |
| 5,114,942 A | * 5/1992 | Gawin et al. ................ | 514/255 |
| 5,726,190 A | * 3/1998 | Rose et al. .................. | 514/282 |
| 6,004,970 A | * 12/1999 | O'Malley et al. ........... | 514/282 |

FOREIGN PATENT DOCUMENTS

| | | | |
|---|---|---|---|
| EP | 0 204 954 B1 | 7/1992 | ......... A61K/31/135 |

OTHER PUBLICATIONS

Spealman; "Antagonism of behavioral effects of cocaine by selective dopamine receptor blockers"; *Psychopharmacology* 101(1):142–145; 1990.

O'Brien; "Rat Study Sheds Light on Cocaine Craving"; *Science* 271(5254):1499; Mar. 8, 1996.

Cervo et al.; "Effects of dopaminergic and glutamatergic receptor antagonists on the acquisition and expression of cocaine conditioning place preference"; *Brain Research* 673;242–250; 1995.

Spealman et al.; "Discriminative Stimulus Effects of Cocaine in Squirrel Monkeys: Involvement of Dopamine Receptor Subtypes[1]"; *The Journal of Pharmacology and Experimental Therapeutics* 253(3):945–953; 09/91.

Spealman et al.; "Differential modulation of behavioral effects of cocaine by low– and high–efficacy $D_1$ agonists"; *Psychopharmacology* 133:283–292; 1997.

Winger; "Dopamine antagonist effects on behavior maintained by cocaine and alfentanil in rhesus monkeys"; *Behavioural Pharmacology* 5(2):141–152; 04/1994.

Baker et al.; Time course analysis of the discriminative stimulus effects of the optical isomers of 3,4–methylene–dioxymethamphetamine (MDMA); *Pharmacology Biochemistry and Behavior* 58(2):505–516; 1997.

West et al.; "Stimulus Effects of d–Amphetamine II: DA, NE, and 5–HT Mechanisms"; *Pharmacology Biochemistry and Behavior* 51(1):69–76; 1995.

Acquas et al.; "D1 receptor blockade stereospecifically impairs the acquisition of drug–conditioned place preference and place aversion"; *Behavioural Pharmacology* 5(6):555–569; 1994.

H. Breiter et al.; "Acute Effects of Cocaine on Human Brain Activity and Emotion"; Neuron 19:591–611; Sep. 1997.

Y. Chen et al.; "Detection of Dopaminergic Neurotransmitter Activity using Pharmacologic MRI: Correlation with PET, Microdialysis, and Behavioral Data"; Magnetic Resonance in Medicine 38/3:389–398; Sep. 1997.

Chou et al.; "The Influence of Halothane on Cocaine–Induced Regional Brain Activation: a 2DG Study"; Society for Neuroscience (Abstracts); 27th Annual meeting; vol. 23, Part 1, 314.1, p. 803; Oct. 1997.

Fremeau et al.; "Localization of $D_1$ dopamine receptor mRNA in brain supports a role in cognitive, affective and neuroendocrine aspects of dopaminergic neurotransmission"; Proc. Natl. Acad. Sci. USA 88:3772–3776 (1991).

Gawin; "Cocaine Addiction: Psychology and Neurophysiology"; Science 251/5001:1580–1586; Mar. 1991.

Gold et al.; "Cocaine Abuse: Neurochemistry, Phenomenology, and Treatment"; Cocaine Use in Epidemiologic Clinical Perspectives; Kozel, NJ, Adams EH, eds.; pp. 130–150 (1985).

Gollub et al. Cocaine Decreases Cortical Cerebral Blood Flow But Does Not Obscure Regional Activation in Functional Magnetic Resonance Imaging in Human Subjects; J. Cereb. Blood Flow Metab. 18:724–734 (1998).

Hemby et al.; "Assessment of the Relative Contribution of Peripheral and Central Components in Cocaine Place Conditioning"; Pharmacology Biochemistry and Behavior 47/4:973–979 (1994).

(List continued on next page.)

Primary Examiner—Dameron L. Jones
(74) Attorney, Agent, or Firm—Fish & Richardson P.C.

(57) ABSTRACT

The invention provides methods for inhibiting psychostimulant-induced or nicotine-induced craving of additional psychostimulants (e.g., cocaine or amphetamine) or nicotine. In these methods, D1-like antagonists or D1-like agonists are administered to a patient dependent on psychostimulant drugs or nicotine and therefore susceptible to, or suffering from, such a craving. Also disclosed is an animal model system useful for measuring the ability of test compounds to inhibit pyschostimulant-induced or nicotine-induced cravings in humans.

20 Claims, 9 Drawing Sheets

OTHER PUBLICATIONS

Jung et al.; Physical properties of MION–46 and AMI–227, Int. Soc. Magn. Reson. Med., 4th Annual Meeting New York, NY 1996; p. 1681.

Koob et al.; "Cellular and Molecular Mechanisms of Drug Dependence"; Science 242:715–723 (Nov. 1988).

Koob et al.; "The Neurobiology of Drug Addiction"; The Journal of Neuropsychiatry 9/3:482–497 (1997).

Ogawa et al.; "The Sensitivity of Magnetic Resonance Image Signals of a Rat Brain to Changes in the Cerebral Venous Blood Oxygenation"; Mag. Reson. Med. 29:205–210 (1993).

Ogawa et al.; "Functional brain mapping by blood oxygenation level–dependent contrast magnetic resonance imaging"; Biophysical Journal 64:803–812 (1993).

Payen et al.; "Regional Cerebral Plasma Volume Response to Carbon Dioxide Using Magnetic Resonance Imaging"; Anesthesiology 88/4:984–992 (1998).

Self et al.; "Molecular Mechanisms of Drug Reinforcement and Addiction"; Annu. Rev. Neurosci. 18:463–495; (1995).

Sharkey et al.; "Acute cocaine administration: effects on local cerebral blood flow and metabolic demand in the rat"; Brain Research 548:310–314 (1991).

Stein et al.; "Selective Effects of Cocaine on Regional Cerebral Blood Flow in the Rat"; The Journal of Pharmacology and Experimental Therapeutics 262/1:327–334 (1992).

Stein et al., "Cocaine's time action profile on regional cerebral blood flow in the rat"; Brain Research 626:117–126 (1993).

Johanson et al.; "The Pharmacology of Cocaine Related to Its Abuse"; Pharmacological Reviews 41/1:3–52 (1989).

Kwong et al., "Dynamic magnetic resonance imaging of human brain activity during primary sensory stimulation" Proc. Natl. Acad. Sci., USA 89:5675–5679 (1992).

Ogawa et al.; "Intrinsic signal changes accompanying sensory stimulation: Functional brain mapping with magnetic resonance imaging"; Proc. Natl. Acad. Sci. USA 89:5951–5955 (1992).

Bandettini et al.; "Time Course EPI of Human Brain Function during Task Activation"; Magnetic Resonance in Medicine 25:390–397 (1992).

Fischman et al.; "Cocaine self–administration in humans"; Federation Proceedings 41/2:241–246 (1982).

Fischman et al.; "Acute Tolerance Development to the Cardiovascular and Subjective Effects of Cocaine"; The Journal of Pharmacology and Experimental Therapeutics 235/3: 677–682 (1985).

Foltin et al.; "Smoked and Intravenous Cocaine in Humans: Acute Tolerance, Cardiovascular and Subjective Effects"; The Journal of Pharmacology and Experimental Therapeutics 257/1:247–261 (1991).

Breiter et al.; "Functional Magnetic Resonance Imaging of Symptom Provocation in Obsessive–compulsive Disorder"; Archives of General Psychiatry 53:595–606 (Jun. 1996).

Vogt et al.; Topography of Diprenorphine Binding in Human Cingulate Gyrus and Adjacent Cortex Derived From Coregistered PET and MR Images; Human Brain Mapping 3:1–12 (1995).

Breiter et al.; "FMRI of Effortful Attention Using Talairach Averaging Across Subjects"; [Abstract]; Proc. Soc. Magn. Reson./Euro. Soc. Magn. Reson. Med. Biol. Joint Meeting 3:1348 (1995).

Breiter et al.; "Response and Habituation of the Human Amygdala during Visual Processing of Facial Expression"; Neuron 17/5:875–887 (Nov. 1996).

Mandeville et al.; "Dynamic Liver Imaging with Iron Oxide Agents: Effects of Size and Biodistribution on Contrast"; Magnetic Resonance in Medicine 37/6:885–890 (Jun. 1997).

Ayata et al.; "L–NA–Sensitive rCBF Augmentation During Vibrissal Stimulation in Type III Nitric Oxide Synthase Mutant Mice"; Journal of Cerebral Blood Flow and Metabolism 16/4:539–541 (1996).

Mandeville et al.; "Dynamic Functional Imaging of Relative Cerebral Blood Volume During Rat Forepaw Stimulation"; Magnetic Resonance in Medicine 39/4:615–624 (1998).

* cited by examiner

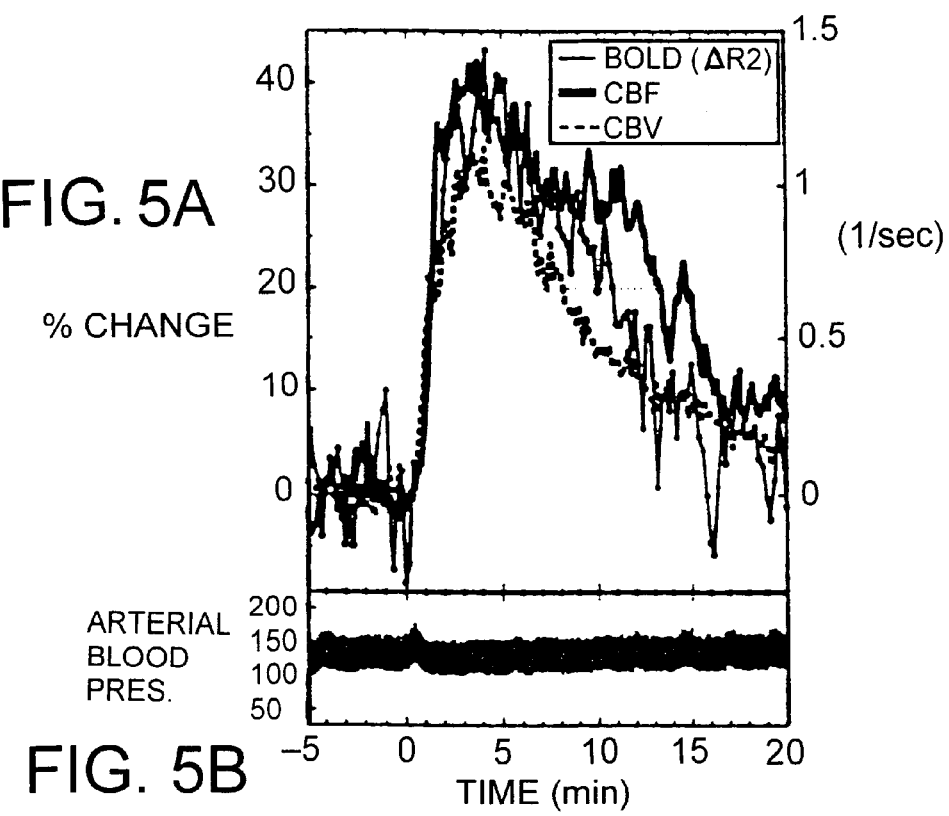
FIG. 5A
FIG. 5B
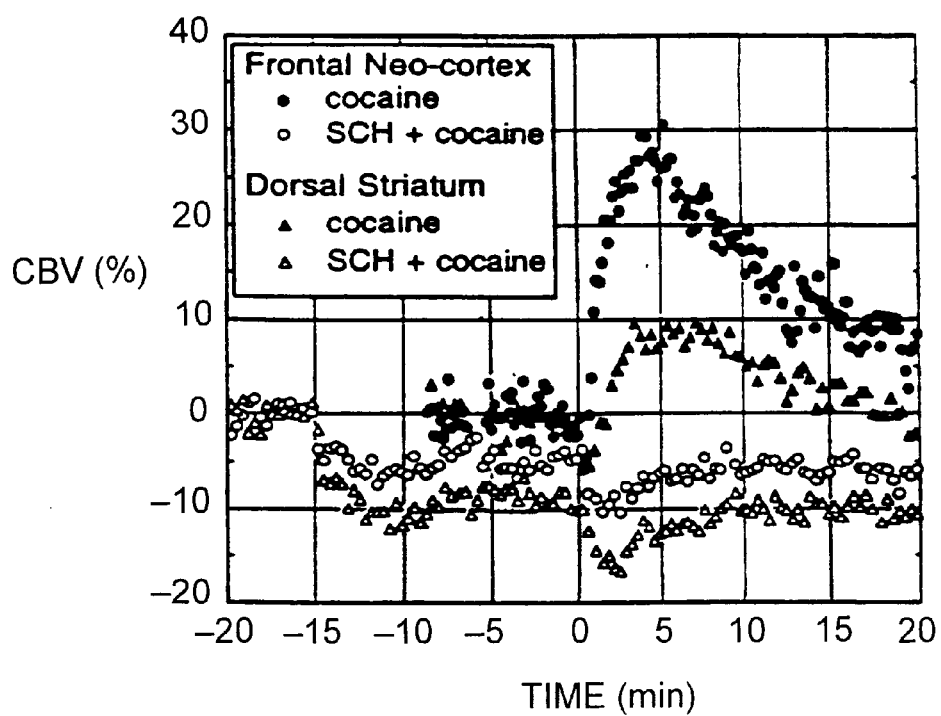
FIG. 9

% Increase CBV

INHIBITION OF PSYCHOSTIMULANT-INDUCED AND NICOTINE-INDUCED CRAVING

CROSS-REFERENCE TO RELATED APPLICATION

This application claims priority under 35 U.S.C. §119 from U.S. Ser. No. 60/059,838, filed Sep. 24, 1997.

STATEMENT AS TO FEDERALLY SPONSORED RESEARCH

The research described herein was supported, at least in part, with funds from the Federal Government awarded through the National Institute of Drug Abuse (under grants DA00265-02, DA00275-02, and DA09467-03), and through the Heart, Lung and Blood Institute of the National Institutes of Health (under grant #39810). The Government therefore may have certain rights in the invention.

BACKGROUND OF THE INVENTION

This invention relates to inhibition of psychostimulant-induced or nicotine-induced craving in humans.

The use of psychostimulants, such as cocaine, and of nicotine often leads to repeated use and a profound state of addiction in humans, which is characterized by compulsive drug use and an inability to control use despite significant adverse consequences. Cocaine, for example, is one of the most reinforcing drugs known (Johanson et al., 1989, Pharmacol. Rev. 41:3–52). Progress toward understanding the neural substrates of addiction to cocaine and other addictive drugs has mostly been limited to research with animal models. The use of such animal models, however, has been limited by the inability to correlate observed patterns of brain activation with subjective information about emotional and cognitive responses to drugs, such as euphoria or craving typically experienced after use of addictive drugs.

SUMMARY OF THE INVENTION

It has now been shown that a distinct pattern of brain activation is exhibited by humans during periods of craving induced by a psychostimulant. As determined by functional magnetic resonance imaging (fMRI), psychostimulant-induced craving (e.g., cocaine-induced craving) is strongly correlated with early, but sustained, signal changes (positive or negative) in the nucleus accumbens and in the amygdala. In contrast, as shown below, the cocaine-induced experience of rush is associated with a pattern of brain activation distinct from the pattern exhibited during cocaine-induced craving. As discussed in further detail below, the studies described herein demonstrate that (a) humans have the same extended neural network of reward circuitry as animals, and (b) this circuitry performs both reinforcement reward and incentive reward function (e.g., craving). These observations, along with (1) observations from animal studies, showing that drugs specific for D1 receptors alter reward processes in the brain and (2) observations regarding the distribution of dopamine receptor subtypes in the brain, indicate that agonists and antagonists of the D1-like receptors can be used to inhibit craving of psychostimulants in humans, with or without inhibition of euphoria. In addition, such agonists and antagonists can be used to inhibit craving of the stimulant nicotine, which is associated with intense craving and is predicted to induce patterns of brain activation that parallel those seen with psychostimulants such as cocaine.

Without being bound to any particular theory or mechanism, D1-like agonists (also referred to herein as "D1-like receptor agonists") are thought to provide some or all of the sensations of rush and high associated with the use of a psychostimulant or nicotine, without leading to significant levels of further drug craving. Although a patient treated with a D1-like agonist may consume an initial quantity of a psychostimulant or nicotine, further craving of the addictive drug will be inhibited, thereby inhibiting binge-like drug consumption. D1-like antagonists are thought to inhibit initial cravings for psychostimulants or nicotine or to reduce the euphoria felt from psychostimulants or nicotine, thereby inhibiting the initiation of binge-like behavior.

Accordingly, the invention features a method for inhibiting a psychostimulant-induced craving in a human, which method entails identifying the human as being psychostimulant-dependent, and administering to the human a D1-like antagonist or D1-like agonist in an amount effective to inhibit craving of the psychostimulant. In various embodiments, the psychostimulant may be cocaine (including crack cocaine) or amphetamine.

In a related method, the invention features a method for inhibiting a nicotine-induced craving in a human, which method entails identifying the human as being nicotine-dependent, and administering to the human a D1-like antagonist or D1-like agonist in an amount effective to inhibit craving of nicotine (e.g., craving of nicotine-containing cigarettes). Typically, in practicing the methods of the invention, the patient (i.e., human) is a compulsive user of the psychostimulant or nicotine. The methods of the invention are particularly useful in inhibiting drug-induced craving, which is the craving experienced after drug use (e.g., within 15 seconds to 120 minutes).

Now that, as shown by the experiments described below, the psychostimulant-induced patterns of brain activation in humans and rodents are known to overlap each other closely, rodents (e.g., rats and mice (including knockout mice, such as knockouts of the D1 receptor or DAT transporter)) can be used as animal model systems for measuring the ability of a test compound to inhibit psychostimulant-induced or nicotine-induced craving in a human. This method of the invention entails administering the test compound to a rodent; administering a psychostimulant or nicotine to the rodent; and measuring an attenuation in the level of brain activation in the rodent subsequent to administration of (a) the test compound and (b) the psychostimulant or nicotine, as compared with the level of brain activation obtained upon (a) administration of the psychostimulant or nicotine to the rodent without (b) administration of the test compound, as a measure of the ability of the test compound to inhibit psychostimulant-induced or nicotine-induced craving in a human. In various embodiments, the psychostimulant can be cocaine (including crack cocaine) or amphetamine. The animal may be drug-naive, or it may be chronically addicted to a psychostimulant or nicotine by virtue of its having been repeatedly treated with the drug previously. Useful animal models of chronic addiction include, without limitation, (a) animals taught to self-administer drugs and (b) condition-place preference paradigms (where the readiness of an animal to go to a place where the animal has previously had the drug is measured). The test compound can be a known D1-like agonist or D1-like antagonist (such as those described herein), or it may be any compound of interest, such as uncharacterized small organic molecules of interest. The test compound typically is administered at a dosage of 0.0001 to 100 mg/kg of the body weight of the rodent.

Typically, the test compound is administered to the animal 0 minutes to 2 days (e.g., 15 minutes to 8 hours) prior to administration of the psychostimulant or nicotine to the animal. The test compound can be administered to the animal in a single dose or in repeated doses (e.g., 1, 2, or 5 or more times daily) prior to administration of the psychostimulant or nicotine. The decrease in the level of brain activation can be measured by any of the various methods for measuring brain activations, such as functional MRI (with or without contrast agents such as monocrystalline iron oxide nanocolloid (MION) particles or gadolinium) and laser Doppler-flowmetry, as described above for example.

Examples of suitable D1-like antagonists for use in the methods of the invention include SCH 39166; SCH 23390; A-69024; bulbocapnine; butaclamol HCl, (+)-; fluphenazine HCl; flupenthixol 2 HCl, cis-(Z)-, fluspirilene; haloperidol; SCH-12679; SKF-83566; thioridazine HCl; thiothixine HCl; trifluoperazine 2HCl; and trifluorperidol HCl. Examples of suitable D1-like agonists include A-86929; 6-chloro-PB HBr, (±)-(SKF 81297); SKF 38393; A-69024, N-allylnorapomorphine HBr, R(-)-; apomorphine HCl, R(-)-; 6-bromo-APB HBr, r(+)-; 6-Chloro-APB HBr,(±)- (SKF-82958); Pergolide methanesulfonate, and SKF 77434. Such agonists or antagonists can be administered to the patient or animal at a dosage of 0.0001 mg/kg to 100 mg/kg of the body weight of the patient or animal, and more typically at a dosage of 0.1 to 1.0 mg/kg of the body weight of the patient or animal. In a typical method of administration, the D1-like antagonist or D1-like agonist is administered to the patient or animal orally, intravenously, or intramuscularly. Typically, an initial dosage of the D1-like antagonist or D1-like agonist will be administered to the patient within 0 to 24 hours of consumption of a psychostimulant or of nicotine by the patient, and potentially continued with a daily dose(s) for 1 to 365 days, or even life-long if desired.

A "psychostimulant" is any agent having antidepressant or mood-elevating properties in a human, such as amphetamine and cocaine, or producing reinforcing effects during drug self-administration paradigms or conditioned-place preference paradigms in non-human animals.

A "compulsive" psychostimulant or nicotine user is a person who has an irresistible impulse or strong craving to use a psychostimulant or nicotine, which typically is manifested as repetitive self-administration of the psychostimulant or nicotine.

A "D1-like agonist" is any compound that activates signal transduction via D1-like dopamine receptors or D1 dopamine receptors, typically by reversibly binding with its receptor and often with the resultant effect that is proportional to the number of receptors occupied. D1 agonists are encompassed by the term D1-like agonists as used herein.

A "D1-like antagonist" is any compound that interacts with D1-like or D1 dopamine receptors, or with other components of the D1 effector mechanism, to inhibit the action of an agonist while initiating no effect itself. D1 antagonists are encompassed by the term D1-like antagonists as used herein.

"Craving" is a monofocused motivational state, which occurs in the context of a perceived deficit of a reward. The degree of craving can be measured in terms of the behavior the person is willing to implement to get the objective of their motivational state.

The invention offers several advantages. By providing a method for inhibiting drug-induced craving, the invention provides an effective method for treating drug addictions (e.g., cocaine addiction). Because D1-like receptors are preferentially localized to the regions of the brain that mediate drug-induced craving (e.g., the nucleus accumbens and the amygdala), the use of D1-like agonists and antagonists provide specificity in targeting the appropriate regions of the brain. By using D1-like agonists in treating a patient, the patient may experience some sensations that are similar to those achieved through the use of the addictive drug (e.g., rush and high), without experiencing the withdrawal-related craving associated with cessation of drug use. The patient can experience non-psychostimulant-induced euphoria and/or reward, along with forming emotional memories of these experiences.

Other features and advantages of the invention will be apparent from the following detailed description, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

BRIEF DESCRIPTION OF THE DRAWINGS

FIG. 5A is a graph illustrating a temporal response of CBF, cerebral blood volume (CBV), and BOLD signal after infusion of 0.5 mg/kg cocaine determined in approximately the same anatomical region of frontal cortex. Data are presented as percent CBF measured by LDF (n=6), percent CBV determined by MRI with monocrystalline iron oxide nanocolloid (MION) contrast (n=4) (other agents that have an effect on magnetic relaxation also can be used), and $R_2$ for BOLD (n=5). Cocaine was infused at Time=0 minutes. Responses in CBF, CBV and $R_2$ were calculated relative to the average value for the 5 minute baseline period (−5 to 0 minutes) immediately before cocaine infusion; time courses represent average responses. Averaged baseline standard deviation was ±1.9% for CBF; ±1.4% for CBV; ±0.15 for $R_2$. FIG. 5B is a graph of representative temporal response in arterial blood pressure due to infusion of 0.5 mg/kg cocaine for an individual rat.

FIG. 9 is a graph representing a time course of CBV response in frontal neocortex (circles) and dorsal striatum (triangles) after 0.5 mg/kg cocaine infusion in rats either pretreated with 0.1 mg/kg SCH-23390 (closed circle and closed triangles) or without pretreatment (open circles and open triangles). In both animals, cocaine infusion was initiated at Time=0; the pretreated rat received SCH-23390 15 minutes before cocaine infusion (Time=−15). Responses were calculated relative to the average CBV during the 5 minute baseline period immediately preceding drug infusion (−5 to 0 minutes in the non-pretreated animal and −20 to −15 minutes in the SCH-23390 pretreated animal).

DETAILED DESCRIPTION

Figure 1:
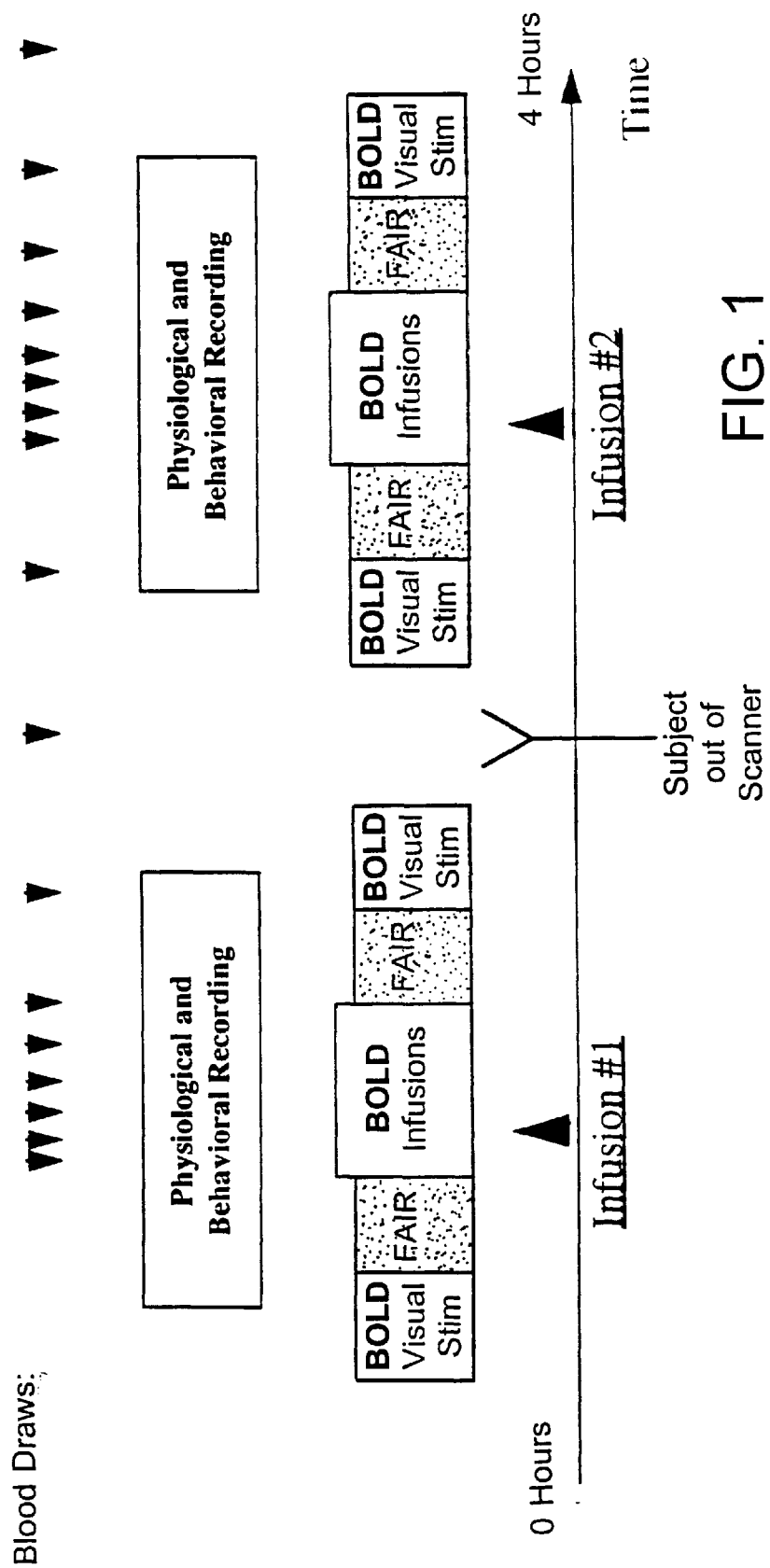
FIG. 1 is a schematic representation of the design of experiments described herein. Over a 5 hour period, subjects participated in 10 experimental fMRI scans. The experimental runs were grouped, 5 apiece, around each of the double-blind infusions. Physiological recording along with behavioral ratings were initiated prior to the first flow-sensitive alternating inversion recovery (FAIR) scan and continued through the second FAIR scan of each infusion block. After the first infusion, the second double-blind infusion could not be initiated until the 120 minute blood sample had been collected. In between the sets of functional scans for each infusion, clinical scans were acquired for neuroradiological assessment. These scans included: sagital T1 images, axial proton density, and T2 images, and 3D time-of-flight angiogram.

The invention provides methods for inhibiting in a human a psychostimulant-induced or nicotine-induced craving for additional psychostimulants or nicotine. By inhibiting such a drug-induced craving, the binge-like behavior typically associated with the use of addictive drugs (e.g., cocaine, amphetamine, or nicotine) can be inhibited. Preferred candidates for treatment in accordance with the invention are patients who are psychostimulant-dependent or nicotine-dependent. Generally, the typical patient is susceptible to, or suffering from, a psychostimulant-induced or nicotine-induced craving; such patients can be identified simply on the basis of their having consumed a psychostimulant or nicotine in the 30 seconds to 120 minutes prior to administration of a D1-like agonist or antagonist to the patient. Typically, the patient is a compulsive user of a psychostimulant or of nicotine. In an alternative method, the pattern of brain activation in the patient (as determined, for example, by fMRI as described herein) indicates that the patient is suffering from a craving induced by a psychostimulant or nicotine (e.g., sustained signal maxima in the nucleus accumbens and negative signal changes in the amygdala).

Once a patient is identified as being psychostimulant-dependent or nicotine-dependent (and therefore susceptible to, or suffering from, a psychostimulant-induced or nicotine-induced craving), a D1-like antagonist or D1-like agonist is administered to the patient in an amount effective to inhibit the craving. Examples of suitable D1-like antagonists include, without limitation, SCH 39166; SCH 23390; SCH 23388; A-69024; bulbocapnine; butaclamol HCl, (+)-; fluphenzanine HCl; fluphenthixol 2 HCl, cis-(Z)-, fluspirilene; haloperidol; SCH-12679; SKF-83566; thioridazine HCl; thiothixine HCl; trifluoperazine 2HCl; and trifluorperidol HCl. Examples of suitable D1-like agonists include A-86929; 6-chloro-PB HBr, (±)-(SKF 81297); SKF 38393; A-69024, N-allylnorapomorphine HBr, R(−)-; apomorphine HCl, R(−)-; 6-bromo-APB HBr, r(+)-; 6-Chloro-APB HBr, (±)-(SKF-82958); Pergolide methanesulfonate, and SKF 77434. Other D1-like antagonists and D1-like agonists are known in the art and can be used in practicing the invention. Such agonists and antagonists, as well as additional suitable agonists and antagonists, are available from commercial suppliers such as Research Biochemicals International. Conventional methods can be used to identify additional D1-like antagonists and D1-like agonists, which also can be used in practicing the invention. If desired, the D1-like antagonists and agonists can be used in combination (e.g., at a ratio from 1:1 up to 10:1).

D1-like antagonists and D1-like agonists can be formulated for administration to the patient by any of a variety of known routes. For example, solid formulations of the D1-like antagonists or D1-like agonists for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the D1-like antagonists or D1-like agonists for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

Injectable formulations of the D1-like agonists and D1-like antagonists may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the D1-like agonist or D1-like antagonist and a physiologically acceptable excipient is infused into the patient. Physiologically acceptable excipients include, for example, 5% dextrose, 0.9% saline, Ringer's solution or other suitable excipients. For intramuscular preparations, a sterile formulation of a suitable soluble salt form of the agonist or antagonist can be dissolved and administered in a pharmaceutical excipient, such as Water-for-Injection, 0.9% saline, or 5% glucose solution.

The optimal concentration of the D1-like antagonist or D1-like agonist in each pharmaceutical formulation varies according to the formulation itself. Typically, the pharmaceutical formulation contains the agonist or antagonist at a concentration of about 0.1 to 90% by weight (such as about 1–20% or 1–10%). Appropriate dosages of the D1-like antagonist or D1-like agonist can readily be determined by those of ordinary skill in the art of medicine by assessing inhibition of drug-induced craving in the patient, and increasing the dosage and/or frequency of treatment as desired. The optimal amount of the D1-like antagonist or agonist for inhibiting craving of a psychostimulant or nicotine may depend upon the mode of administration, the age and the body weight of the patient, and the condition of the patient. Typically, a D1-like antagonist is administered at a dosage of 0.001 to 100 mg/kg of body weight of the patient; e.g., the antagonist is administered at a dosage of 0.1 to 1.0 mg/kg. A D1-like agonist typically is administered at a dosage of 0.001 to 100 mg/kg of body weight of the patient, e.g., at a dosage of 0.1 to 1.0 mg/kg.

In a typical method of treatment, the patient is a compulsive user of a psychostimulant or nicotine. Treatment of an addiction to a psychostimulant or nicotine thus generally involves a regimen in which a D1-like antagonist or D1-like agonist is repeatedly administered to the patient. Typically, the D1-like antagonist or D1-like agonist is administered to the patient once every two days, once daily, or even more frequently to alleviate the drug dependency, and typically over a time span of about 1 to 12 months or even life-long if needed.

EXAMPLES

For the following examples, in vivo studies were conducted with human cocaine users, and with rats that were treated with cocaine. To identify the circuitry active in human brains during cocaine infusions, and to associate this activity with subjective reports for both cocaine-induced euphoria and post-cocaine craving, functional Magnetic Resonance Imaging (fMRI; Kwong et al., 1992, Proc. Natl. Acad. Sci. 89:5675–5679; Ogawa et al., 1992, Proc. Natl. Acad. Sci. 89:5951–5955; Bandettini et al., 1992, Magn. Reson. Med. 25:390–397) was used in conjunction with physiological monitoring and online evaluation of computerized behavioral rating scales. The fMRI data obtained from subsequent studies conducted with rats, when compared with data obtained from humans, showed a notable overlap in the pattern of cocaine-induced activation of subcortical structures. In rats, cocaine-induced brain activation was completely blocked by administration of the D1 antagonist SCH-233390 prior to administration of cocaine. These studies indicate that the D1 receptor mediates the acute action of cocaine, and these studies support the conclusion that D1-like agonists and D1-like antagonists can be used to inhibit craving of psychostimulants, and of nicotine. These studies also show that an animal model can be used to measure the ability of a test compound to attenuate psychostimulant-induced or nicotine-induce brain activations and thereby inhibit craving. An exemplary animal model system is described below.

Example 1

Human Studies

For the experiments with humans, cocaine-dependent volunteers underwent an unblinded cocaine infusion the night before the fMRI experiment for clinical screening, and for training with behavioral assessments on scales of rush, high, low and craving. During the subsequent double-blind cocaine (0.6 mg/kg) and saline infusions, subjects rated these four scales every 15 seconds during multiple fMRI acquisitions (FIG. 1). In these experiments, blood oxygen level dependent (BOLD) signal changes (Ogawa et al., 1992, Proc. Natl. Acad. Sci. 89:5951–5955) were measured after infusions of cocaine and saline, separately, into patients. Briefly, the following data show that infusion of cocaine induced BOLD signal changes (i.e., "activations"), whereas few activations were detected after infusion of saline. Following infusion of cocaine, patients exhibited dynamic patterns of brain activation over time as the patient experienced sensations of rush, high, low, and drug-induced craving. A distinct pattern of brain activation is exhibited as patients experienced drug-induced craving. The brain regions exhibiting positive or negative activations during drug-induced craving (the nucleus accumbens and amygdala in particular) contain high levels of D1-like receptors. Compounds that alter the function of these receptors in the nucleus accumbens and/or amygdala (i.e., D1-like agonists and antagonists) can now be used to inhibit drug-induced craving, and inhibit binge-like consumption of addictive drugs such as psychostimulants and nicotine.

1. Clinical and Physiological Data

Seventeen subjects were infused with cocaine while being scanned with fMRI. Scans affected by uncorrectable gross movement were rejected as uninterpretable. Of these 17 subjects, 10 had interpretable fMRI data for the cocaine infusions and 10 had interpretable data for the saline infusions after motion-correction (7 studies with usable matched infusions).

Following the cocaine infusion (0.6 mg/kg over 30 seconds), there was an increase in heart rate (HR) within the first minute, while the increase in mean blood pressure (MBP) was slower. Similarly, the drop in end-tidal carbon dioxide (ETCO$_2$) was also slower. Cocaine (n=17) caused the HR to increase rapidly from a pre-infusion value of 60±7 beats per minute (bpm) to 79±16 bpm at 2 minutes post-infusion (p<0.0001), to 82±12 bpm at 5 minutes post infusion (p<1×10$^{-6}$), to 93±14 bpm at 10 minutes post infusion (p<1×10$^{-8}$). Normal sinus rhythm was observed in all subjects throughout the study.

The mean blood pressure rose slightly, from 96±12 torr before the infusion, to 101±12 torr at 2 minutes post-infusion (p<0.11, N.S.), then up to 111±15 torr at 5 minutes (p<0.002) before starting to slowly decline. The ETCO$_2$ dropped slowly from a baseline of 39±4 mm Hg to 36±4 mm Hg by 10 minutes (p<0.02). In all subjects scanned, these three measures had returned to baseline by 2 hours, the inter-infusion interval (Gollub et al., 1996, Proc. Soc. Neuroscience 3:1933). These physiologic responses to the 0.6 mg/kg cocaine infusion are in close accord with previously published studies in experienced cocaine abusers (Fischman et al., 1982, Fed. Proceed 41:241–246; Fischman et al., 1985, J. Pharm. Exper. Ther. 235:677–682; Foltin et al., 1991, J. Pharm. Exper. Ther. 257:247–261).

Plasma samples taken before the first infusion demonstrated an absence of residual cocaine at the time of the first infusion in all of the subjects studied. Peak plasma cocaine levels (Cmax) following the cocaine infusion ranged from 197 to 893 mcg/L with a mean of 388.7±233.0 mcg/L (n=7 subjects with complete data). The time to peak cocaine plasma concentration varied from 3 to 15 minutes for subjects in the initial series of experiments (mean±SD: 7.6±4.2 min) and the 4 subjects with interpretable re-test experiments (mean±SD: 6.0±2.9 min).

Scores for the Profile of Mood States (POMS) inventory, assessed before, in-between, and after the two infusions, showed no change in five of the six POMS measures (i.e., tension, depression, vigor, fatigue, confusion) over the total scan time. Vigor increased in the second infusion for both cocaine and saline infusions. Spielberger scores assessed before, between, and after both infusions indicated no significant change in anxiety levels across scans. These observations are consistent with the interpretation that subjects did not experience increased discomfort or anxiety in the scanner environment over the course of the experiment.

2. Behavioral Measures

Figure 2:
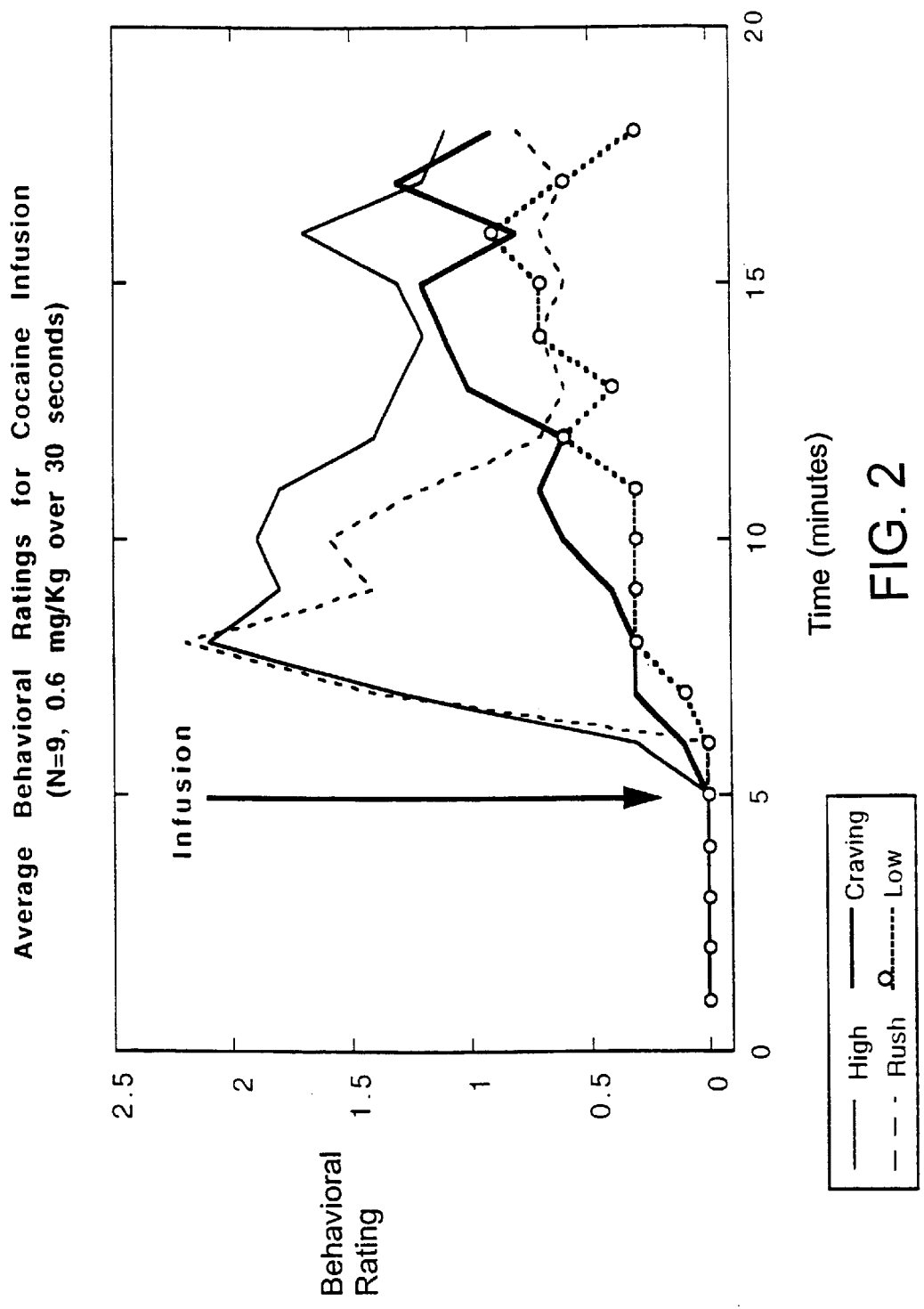
FIG. 2 is a graph of average behavioral ratings. The rush, high, low and craving ratings were averaged within each category for the 9 of 10 subjects who had interpretable cocaine fMRI data after motion correction, and behavioral ratings time-locked to the scanner.

All 10 subjects with interpretable cocaine fMRI data reported clear cocaine effects (see FIG. 2). Both the peak rush (max score=3; mean±SD=2.2±1.1) and the peak high (2.1±0.8) occurred, on average, at 3 minutes post-infusion. The peak low (primarily reports of dysphoria and paranoia: 0.9±0.8) occurred at 11 minutes post-infusion; while, peak craving (1.3±0.9) occurred at 12 minutes post-infusion. No subject reported effects from the saline infusion on any of the four measures. The behavioral ratings obtained for rush, high, low, and craving measures at a cocaine dosage of 0.6 mg/kg (under blinded conditions and given in the fMRI scanner) were higher than those obtained at a dosage of 0.2 mg/kg (under unblinded conditions) (rush: 1.2±1.1; high: 1.7±1.2; low: 0.8±0.8; craving: 1.0±1.3). For the four subjects with interpretable test-retest cocaine data, behavioral measures were unchanged on average for the two conditions (retest results, rush: 1.8±1.0; high: 2.3±0.5; low: 1.0±0.8; craving: 1.0±1.2).

3. Cocaine Infusion (a) Foci of Signal Change

As shown on Kolmogorov-Smirnov statistical maps, cocaine caused regional signal changes in the brain (p<7.1× 10$^{-6}$; see Tables 1–4 for multiple limbic and paralimbic regions) in discrete foci in the nucleus accumbens/subcallosal cortex (NAc/SCC), caudate nucleus, putamen, basal forebrain, thalamus, insula, hippocampus, parahippocampal region, cingulate, lateral frontal cortices, lateral temporal cortex, parietal cortex, striate and extrastriate cortices. Regional changes in signal were detected in the amygdala (see Table 4), temporal pole, and medial frontal cortex. Positive signal change was also noted in the vicinity of the ventral tegmentum and the pons.

For most of the positive and negative activations with cocaine, plots of signal intensity versus time indicated that the brain activations had early signal maxima, with a rapid (starting within 1 minute of the signal maxima) decrease toward baseline. Some of the brain activations, however, demonstrated early signal maxima that were sustained at a plateau level for time periods ranging from 5 minutes until the end of the scanning interval. As described below, these differences in time course produced a dynamic pattern of brain activation following infusion of cocaine; positive and negative activations in various regions of the brain were correlated with different behavioral states (e.g., rush, high, low, and craving). To determine the extent to which the averaged data reflects activations common to individual subjects in the study, statistical maps were analyzed for 16 subcortical regions (see FIG. 3 for examples of anatomic definitions, and Tables 1–4 for results) in the 10 subjects used for the average map. The data are presented as the ratio of the number of subjects who showed activation in that structure at a less stringent p-value threshold (p<0.001); (for a description of this type of analysis, see Breiter et al., 1996, Arch. Gen. Psychiatry 53:595–606). The individual data analysis strongly supports the average results in the NAc/SCC, thalamus, hippocampus, insula, cingulate gyrus and parahippocampal gyrus, with 8 or 9 of 10 subjects contributing to the group activation. Other regions including caudate, putamen, basal forebrain, and VT also reflected the majority activation, with 6–8 subjects showing activation.

TABLE 1

Characterization of cocaine effects on fMRI signal in Subcortical Grey Structures

| Anatomic Region | | Tal Coordinates | | | P-value | % Signal Change | Proportion Individuals | Multiple Correlation Analysis | |
|---|---|---|---|---|---|---|---|---|---|
| | R/L | A/P | S/I | | (KS-statistic) | (Pre vs post drug) | (p < 0.001) | Rush | Craving |
| NAc/SCC | R | 6 | 7 | −9 | $7 \times 10^{-6}$ | 1.5 | 9/10 | Ø | + |
| | L | −6 | 13 | 0 | $4 \times 10^{-6}$ | 1.5 | 8/10 | Ø | + |
| Caudate | R | 13 | −3 | 22 | $5 \times 10^{-7}$ | 0.8 | 8/10 | + | − |
| | L | −9 | −3 | 19 | $3 \times 10^{-7}$ | 1.0 | 7/10 | + | Ø |
| Putamen | R | 28 | 7 | −3 | $4 \times 10^{-8}$ | 1.4 | 8/10 | + | − |
| | L | −28 | 7 | −3 | NS ($5 \times 10^{-5}$) | 0.5 | 5/10 | Ø | Ø |

TABLE 1-continued

Characterization of cocaine effects on fMRI signal in Subcortical Grey Structures

| Anatomic Region | | R/L | Tal Coordinates A/P | S/I | P-value (KS-statistic) | % Signal Change (Pre vs post drug) | Proportion Individuals (p < 0.001) | Multiple Correlation Analysis Rush | Craving |
|---|---|---|---|---|---|---|---|---|---|
| BF/GP | | R | 22* | 1* | -6* | NS | Ø | 6/10 | Ø | + |
| | | L | -19 | 0 | -3 | $6 \times 10^{-9}$ | 1.8 | 7/10 | + | - |
| Thalamus | | | | | | | | | | |
| aThal | | R | 3 | -18 | 13 | $6 \times 10^{-8}$ | 0.4 | 8/10 | Ø | Ø |
| | | L | Ø | Ø | Ø | NS | Ø | 7/10 | Ø | Ø |
| pThal | | R | 6 | -25 | 16 | $9 \times 10^{-7}$ | 1.4 | 8/10 | + | Ø |
| | | L | -6* | -31* | 9* | NS | Ø | 8/10 | + | Ø |
| LGN | | R | 19 | -25 | 0 | NS ($8 \times 10^{-5}$) | 0.8 | 8/10 | + | Ø |
| | | L | -19 | -25 | -3 | $2 \times 10^{-7}$ | 0.5 | 7/10 | + | Ø |

TABLE 2

Characterization of cocaine effects on fMRI signal in Temporal Lobe

| Anatomic Region | | R/L | Tal Coordinates A/P | S/I | P-value (KS-statistic) | % Signal Change (Pre vs post drug) | Proportion Individuals (p < 0.001) | Multiple Correlation Analysis Rush | Craving |
|---|---|---|---|---|---|---|---|---|---|
| Hippocampus | | | | | | | | | | |
| aHip | | R | 28* | -18* | -9* | NS | Ø | 9/10 | Ø | - |
| | | L | -28* | -17* | -16* | NS | Ø | 10/10 | Ø | +/- ▽ |
| pHip | | R | 34 | -28 | -13 | $2 \times 10^{-8}$ | 1.8 | 9/10 | + | + |
| | | L | -22 | -37 | 0 | NS ($1 \times 10^{-5}$) | 0.9 | 10/10 | + | Ø |
| Insula | | | | | | | | | | |
| aINS | | R | 34 | 13 | 6 | $3 \times 10^{-8}$ | 0.9 | 10/10 | + | Ø |
| | | L | -28 | 19 | -6 | $5 \times 10^{-6}$ | 0.5 | 8/10 | + | Ø |
| pINS | | R | 41 | -15 | 0 | $2 \times 10^{-9}$ | 1.1 | 8/10 | + | Ø |
| | | L | -41 | -12 | -3 | $3 \times 10^{-11}$ | 1.0 | 7/10 | + | + |
| Amygdala | | R | 22 | -6 | -13 | NS ($-7 \times 10^{-5}$) | -1.2 | 4/10 (+), 5/10 (-) | Ø | - |
| | | L | -25 | -9 | -19 | $-1 \times 0\, 10^{-6}$ | -0.3 | 3/10 (+), 5/10 (-) | Ø | - |

TABLE 3

Characterization of cocaine effects on fMRI signal in Medial Paralimbic Cortices

| Anatomic Region | R/L | Tal Coordinates A/P | S/I | P-value (KS-statistic) | % Signal Change (Pre vs post drug) | Proportion Individuals (p < 0.001) | Multiple Correlation Analysis Rush | Craving |
|---|---|---|---|---|---|---|---|---|
| Cingulate G. | | | | | | | | |
| acG (BA 24/32) | R | 9 | 13 | 34 | $1 \times 10^{-8}$ | 0.9 | 9/10 | + | Ø |
| (BA 32) | R | 3 | 26 | 28 | $3 \times 10^{-7}$ | 0.8 | | + | Ø |
| (BA 24) | B | 0 | -3 | 31 | $3 \times 10^{-8}$ | 1.0 | 9/10 | + | + |
| pCG (BA 31) | R | 3 | -31 | 38 | $3 \times 10^{-6}$ | 0.5 | 8/10 | + | Ø |
| (BA 31) | L | -9 | -28 | 41 | NS ($1 \times 10^{-5}$) | 0.5 | 5/10 | + | + |
| Parahippocampal G. | | | | | | | | |
| (BA 28) | R | 22 | -21 | -22 | $6 \times 10^{-4}$ | 2.7 | 9/10 | + | + + |
| (BA 28) | L | -19 | -28 | -9 | $2 \times 10^{-8}$ | 0.5 | 9/10 | + | + |
| (BA 35) | R | 16* | -40* | -6* | NS | Ø | Ø | + | Ø |
| (BA 19) | L | -30* | -50* | 2* | NS | Ø | Ø | + | + |

TABLE 4

Characterization of cocaine effects on fMRI signal in Brainstem

| Anatomic Region | R/L | Tal Coordinates A/P | Tal Coordinates S/I | P-value (KS-statistic) | % Signal Change (Pre vs post drug) | Proportion Individuals (p < 0.001) | Multiple Correlation Analysis Rush | Multiple Correlation Analysis Craving |
|---|---|---|---|---|---|---|---|---|
| VT (SN) | R | 9 | −15 | −13 | $4 \times 10^{-6}$ | 1.1 | 6/10 | + | ∅ |
|  | L | −16 | −21 | −6 | $3 \times 10^{-9}$ | 1.5 | 6/10 | + | ∅ |

Tables 1–4 summarize activation due to cocaine infusion. 'Anatomic Region' identifies the structure on the basis of subcortical location, lobe, gyrus (if medial paralimbic cortex), or placement in the brainstem. 'BA' indicates the probable Brodmann area, for cortical areas, of activation in the group average data as determined from the atlas of Talairach and Tournoux (1988). Activation laterality is denoted by R and L; when bilateral, a B is used. 'Tal Coordinates' denotes the Talairach coordinates using the atlas of Talairach and Tournoux (1988) of the voxel with the maximum p-value for the KS maps of pre-vs post-infusion time points, and overlapping correlation regions (except where denoted by a *, in which case the coordinates denote the location of the voxel with maximum p-value for the correlational analysis when no significant activation was present in the KS maps of the group average data). Coordinates are expressed in mm from the anterior commissure: R/L, right(+)/left(−); A/P, anterior(+)/posterior(−); SI, superior(+)/inferior(−). 'P-value' indicates the maximum p-value for each activate cluster of voxels on the unsmoothed Kolmogorov-Smirnov statistical map. Regions are listed as significant if $p<7.1\times10^{-6}$. When 'NS' (nonsignificant) is followed by a p-value in parentheses, this indicates a region of activation which did not meet the significance threshold, yet due to symmetric placement with respect to another activation in the opposite hemisphere was included. Percent signal change was determined for each activation by taking all voxels around the max vox with $p<10^{-5}$ and comparing the first 38 fMRI time points with the subsequent 98 time points. 'Proportion Individuals' lists the number of subjects to the total number of subjects (N=10) who showed activation ($p<10^{-3}$ for each voxel) in each anatomically defined region of interest; these regions of interest may include one or more activations from the group average statistical analysis. 'Correlation Analysis' lists the results of a multiple correlational analysis of the fMRI time data to the behavioral measures of rush and craving. A '+' indicates a positive correlation, a '−' indicates a negative correlation, and a 'ø' indicates no correlation to the measure. To be tabulated, a correlation region had to have 5 voxels with R>0.70 for each voxel. The symbol indicates two nearby correlation regions of opposite sign in the same anatomic region. In Table 3, two '+' signs are placed in the craving column for one activation; in this case, one correlation region was correlated to similar degree with both rush and craving measures, while the other correlation region was uniquely correlated to craving alone.

(b) Correlation Maps

Multiple correlation analysis was used to show that the patterns of brain activations observed following cocaine infusion were associated with specific behavioral states. More specifically, this analysis was used to show that early, but sustained, activations in the nucleus accumbens/subcallosal cortex and amygdala are correlated with cocaine-induced craving, rather than cocaine-induced rush.

A correlation value (R) for each behavioral measure was calculated in order to describe the strength of similarity between the signal time course of each brain voxel (i.e., volume element in the fMRI scan) and a particular behavioral measure (e.g., rush, high, low, or craving). Such a correlation between patterns of brain activation and behavioral measures is readily seen between the rush and the craving ratings, which are the most temporally distinct from each other (see FIG. 2).

While rush ratings had early and transient maxima, craving ratings have a longer latency before reaching maximum. The resulting correlation data are summarized in Tables 1–4. Regions of the brain activation that correlated with rush had early and transient signal maxima. Strong correlations were noted for the left basal forebrain and bilateral VT. In addition, many other regions of brain activation on the maps were positively correlated with rush ratings, including sections of the right cingulate gyrus, bilateral insula, bilateral thalamus, bilateral caudate nucleus, bilateral pontine brainstem, and the majority of activations in the prefrontal cortex.

Regions that showed a significant correlation with craving had early signal maxima (or minima for the negative activations), followed by sustained signal change. The sustained signal change in these regions produced a strong correlation with craving. Thus, while the NAc/SCC and amygdala showed early signal changes (positive and negative changes), at the time of rush and high, both regions showed persistent signal changes that correlated significantly with reports of craving but not rush. Another region which showed a positive correlation with craving was a region of the right parahippocampal gyrus.

Other regions of the brain demonstrated a significant correlation with both rush and craving ratings; these regions are identified in Tables 1–4 by a '+' symbol in the columns for both ratings. Of these regions, those that overlapped with activations seen in the comparison of preinfusion versus postinfusion time points include sections of the left parahippocampal gyrus, left cingulate gyrus, left insula, and right hippocampus.

©Test/Retest Comparisons

To confirm the brain activation results described above, seven subjects were retested by infusing cocaine into the patients at times ranging from 3.5 to 4 months after the first experiment. Of these seven subjects, data for four of the subjects was interpretable after infusion of cocaine infusion and motion correction. These four subjects received their double-blind cocaine and saline infusions in the same order for the retest experiments as for the test experiments described above. To keep expectancies as similar as possible between test and retest conditions, subjects were informed on several occasions that the identity of the first retest infusion did not imply the identity of the second retest infusion, and that a double-blind experimental design was maintained for subjects and researchers during all retest infusions. Regions of signal change that were similar between the average brain maps following the test and retest cocaine infusions are listed in Table 5. Regions of brain activation that overlapped had statistical maxima that were within 1.5 cm of each other, or the two activation clusters had overlapping voxels at a high statistical threshold. Twenty-six of thirty-two post-cocaine activations in the test sample were matched by similar activations in the retest experiments, including subcortical regions originally hypothesized to be activated, namely the NAc/SCC, basal forebrain, and caudate. For regions such as the NAc/SCC, the percent signal change for voxels meeting the threshold of $p<10^{-5}$ in the test condition (Left=3.8%, Right=2.4%) was marginally higher than the percent signal change for the retest condition (Left=2.3%, Right=2.1%), though more voxels met the $p<10^{-5}$ threshold on retest. Other areas of activation that matched between test and retest conditions included parahippocampal, thalamic, insular, and cingulate regions.

with the maximum p-values for each activation are within 1.5 cm of each other; thus a '+' is placed in the last column if they are <1.5 cm apart, or a '−' is placed there if they are more than 1.5 cm apart. If there is no overlap, but the max vox of the two activations are within 1.5 cm of each other, the symbol is also placed in the last column.

4. Saline Infusion (a) Foci of Signal Change

As a control, saline was infused into the 10 patients in the initial test group, and fMRI was used to measure brain activations. Saline infusions produced no signal change in the limbic or paralimbic regions. One focus of signal change was noted in the left temporal pole, which approximated a similar activation for the cocaine infusion. For areas outside of the limbic and paralimbic regions, signal changes were noted in the inferior frontal gyrus, inferior/middle temporal gyri, and extrastriate region, and signal changes were noted in the lateral frontal cortex, superior temporal gyri, and extrastriate cortex. Six activations with saline matched the location of activations seen in the cocaine maps.

TABLE 5

Test-Retest Cocaine Infusions: Regions of Similarity for Foci of Positive Signal Change

| | TEST | | | | | RETEST | | | | |
|---|---|---|---|---|---|---|---|---|---|---|
| Anatomy | Tal Coordinate | | | Vox | Anatomy | Tal Coordinate | | | Vox | Proximity |
| (Region/BA) | R/L | A/P | S/I | # | (Region/BA) | R/L | A/P | S/I | # | (<1.5 cm) |
| Subcortical Grey Structures | | | | | | | | | | |
| Caudate/NAc | 25 | −27 | 18 | 8 | Caudate | 18 | −12 | 21 | 77 | − |
| Caudate/NAc | 9 | 15 | −3 | 81 | GO a11 | 3 | 15 | −6 | 160 | + |
| BF/GP | −21 | 0 | −6 | 10 | BF/GP | −15 | 3 | 0 | 23 | + |
| Thalamus/pThal | 6 | −27 | 12 | 62 | Caudate | 18 | −12 | 21 | 77 | − |
| | | | | | Cingulate a23 | 3 | −27 | 28 | 43 | − |
| Temporal Lobe | | | | | | | | | | |
| Lateral and Intrasylvian Surfaces | | | | | | | | | | |
| GTm a21 | 43 | −6 | −15 | 28 | GTm a21 | 46 | −18 | −9 | 26 | +ψ |
| Insula | 37 | −15 | −3 | 38 | | | | | | + |
| Insula | −40 | −15 | −6 | 129 | Insula | −40 | −9 | 0 | 63 | + |
| | | | | | GTm a21 | −46 | −24 | −3 | 57 | + |
| Insula | −40 | 6 | 0 | 45 | Insula | −40 | −9 | 0 | 63 | + |
| Insula | −34 | 12 | 18 | 12 | Insula | −37 | 18 | 6 | 66 | +ψ |
| Medial Paralimbic Cortices | | | | | | | | | | |
| Cingulate a24 | 0 | −3 | 40 | 8 | Cingulate a24 | 3 | 9 | 34 | 83 | + |
| Cigulate a23/31 | 21 | −27 | 34 | 13 | Cingulate a23 | 12 | −18 | 34 | 18 | + |
| | | | | | Cingulate a23 | 3 | −27 | 28 | 43 | − |
| Parahip a35 | 18 | −36 | −12 | 89 | GF a37 | 46 | −51 | −21 | 152 | − |
| | | | | | GF a20/36 | 34 | −33 | −15 | 26 | +ψ |
| Parahip a28/36 | −21 | −24 | −21 | 83 | Thalamus/pThal | −18 | −15 | 3 | 17 | − |
| | | | | | Parahip a35/36 | −28 | −27 | −15 | 150 | + |

Table 5 shows which activations were similar between test and retest conditions for the cocaine infusions. Specific anatomic regions are described using the nomenclature discussed above with the exception of the following terms: GTm (Gyrus temporalis medius), GF (Gyrus Fusiformis), GO (Gyrus Orbitales). 'BA' indicates the probable Brodman area, for cortical areas, of activation. Under 'Coordinates' are the Talairach coordinates (Talairach et al., 1988, New York: Thieme Medical Publishers) of the voxel with the maximum p-value as determined from the KS maps (Breiter et al., 1996, Arch. Gen. Psychiatry 53:595–606). 'Coordinates' are expressed in mm from the anterior commissure: R/L, right(+)/left(−); A/P, anterior(+)/posterior(−); S/I, superior(+)/inferior(−). The number of voxels around the max vox which meet the p-value threshold of $p<10^{-6}$ are listed under 'Vox #'. 'Proximity' lists whether the voxels (b) Test/Retest Comparisons As with the cocaine test/retest comparisons, four of seven subjects had interpretable saline infusion data for test-retest comparison after motion-correction. For the saline test-retest comparison with 4 individuals, no limbic or paralimbic regions were activated. For regions outside of limbic and paralimbic regions, six of the test activations were also similar to those seen during the retest. Of these six activations, four activations approximated activations seen with the average saline map of ten individuals, suggesting that the subgroup of four represent a good approximation of the group of ten.

The saline retest indicated that there were several new activations not detected during the first saline test, the majority of which (10/16) were in the striate, extrastriate, and ventral temporal cortex. Eleven of the sixteen activations were similar to activations seen with the initial cocaine infusion for the total cohort and the retest cocaine infusions in the subgroup of 4 individuals (Table 5). On the basis of location of activation maxima, 11 of the 16 new activations seen during the saline retest infusion in the NAc/SCC, the frontal cortex, and the temporal cortex were seen with either the cocaine test or retest infusions. The activations likely represent a common effect from expectation of cocaine.

Summary of Human Studies

Following an infusion of cocaine under double-blind conditions, subjects reported early maximal behavioral ratings for rush and high at ~3 minutes after cocaine infusion. The maximal ratings for craving and low were reported to occur at 11–12 minutes after cocaine infusion. Cocaine plasma concentrations reached maximum at ~7 minutes after infusion.

Euphoria (Rush): Brain regions that showed focal increases in blood oxygen level dependent signals at the time of onset of euphoria included the NAc/SCC, basal forebrain, and ventral tegmentum, caudate, putamen, thalamus, medial temporal and paralimbic regions (hippocampus, parahippocampal gyrus, cingulate cortex, and insula), brainstem (pons), and neocortical regions, such as the lateral prefrontal cortex, lateral temporal cortex, parietal cortex, and occipital cortex. Changes in fMRI signal were also noted in the amygdala, temporal pole, and medial frontal cortex. In comparison to cocaine, saline produced few regions of fMRI signal changes, which were limited to the lateral prefrontal and temporo-occipital cortex. Small regions of signal change were also noted in the lateral prefrontal cortex and temporal cortex.

Figure 3:
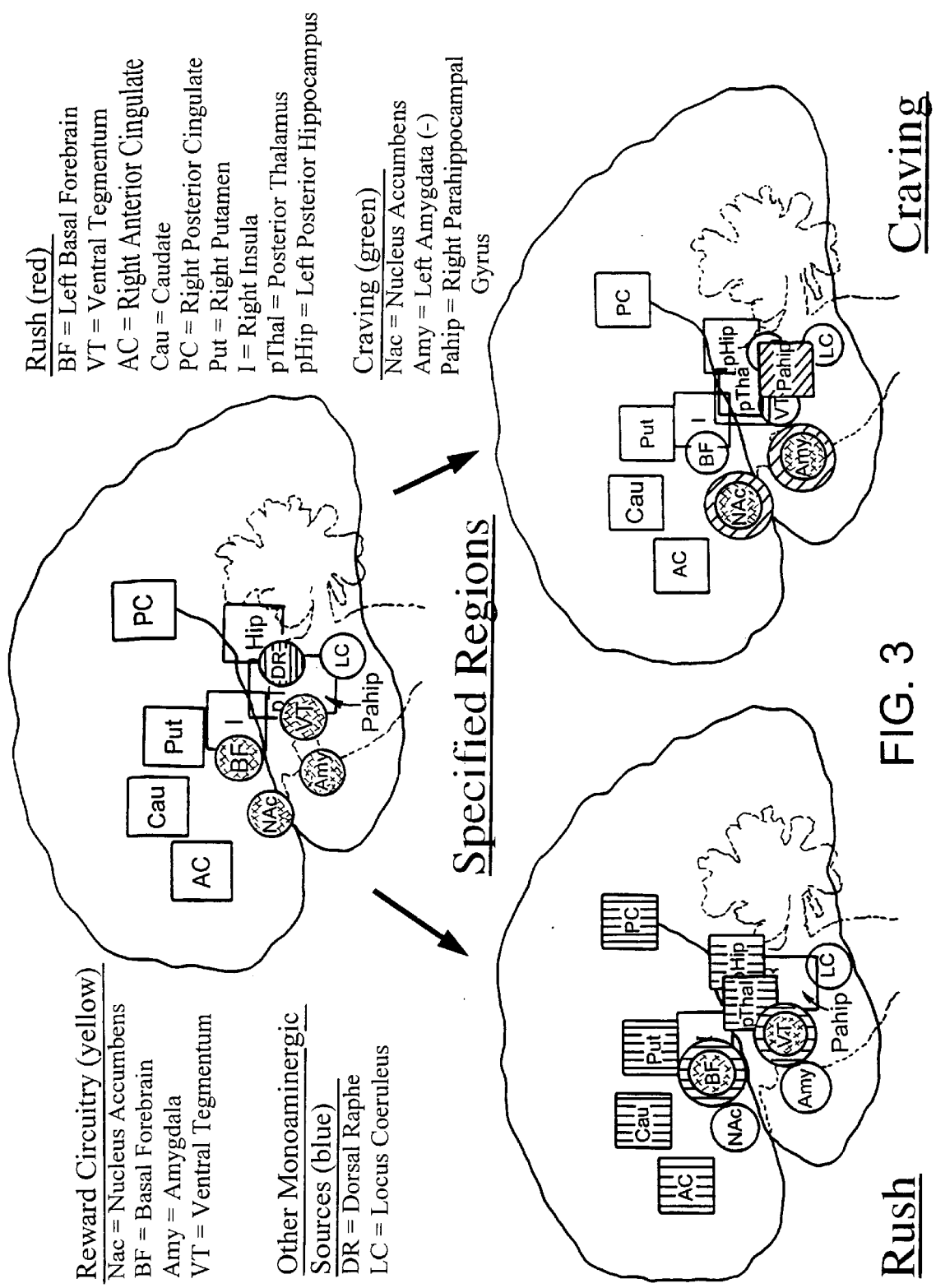
FIG. 3 is a schematic summary of limbic and paralimbic brain regions that correlate with euphoria as compared with those regions that correlate with craving. Above these summary schematics is a schematic of the brain regions predicted to be active after the infusion of cocaine. Two other brainstem monoaminergic regions, potentially encompassed in a pontine activation seen in the baseline vs post-infusion comparison described herein are also illustrated. This pontine activation correlated with behavioral ratings for rush.

Multiple correlational analysis of the averaged behavioral ratings with the averaged cocaine fMRI data indicated differences in the temporal pattern of activation, which can be associated with rush and with craving ratings (FIG. 3). Brain activation correlated with rush ratings was noted in the ventral tegmentum, left basal forebrain, midbrain and pontine brainstem, bilateral caudate nucleus, and right cingulate gyrus. Other brain activations that showed a similar pattern of early and transient signal maxima, included regions of prefrontal, parietal, temporal, and occipital cortex.

Craving: Brain activation that was highly correlated with craving measures was noted in the NAc/SCC and right parahippocampus. A strong correlation with craving was also noted in the amygdala, a region which also showed a significant fMRI signal change on the average brain map. The detection of sustained signal change in the NAc/SCC explains its stronger association with craving, than with rush, ratings. In general, the differences at high thresholds between the rush and craving correlation maps reflect a distinction between behavioral ratings with early peaks and shorter duration (i.e., rush) and ratings with prolonged time courses (i.e., craving). It is significant that subtraction of fMRI time courses with early maxima and short duration from those with prolonged time courses would produce a time course closely resembling that of the craving ratings. This suggests a model for cocaine-induced craving in humans. Craving may not be mediated by one or two distinct brain regions; rather, post-cocaine craving reflects a change over time in the pattern of brain activation from cocaine. Many brain regions are active at the time that subjects report euphoria. Over time, however, only a few brain regions remain activated; this change in the pattern of brain regions activated is associated with the subjective experience of cocaine-induced craving.

Use of D1-like Agonists and Antagonists: As is explained in greater detail above, craving for psychostimulants, such as cocaine and amphetamine, and stimulants such as nicotine, can be inhibited by administering to a patient a D1-like antagonist or D1-like agonist. This conclusion is founded, at least in part, on four observations, three of which show tight homology between animal and human data on the brain circuitry involved with reward, cocaine effects on dopamine neurotransmission for producing reward, and the distribution of dopamine receptor subtypes (e.g., the D1 receptor) in the brain. The fourth observation relates to animal data showing that drugs specific to D1 receptors alter reward processes in the brain.

Based on investigations using rodent and primate models, the mesoaccumbens dopamine pathway, extending from the ventral tegrnentum of the midbrain (VT) to the nucleus accumbens, appears to be the critical shared substrate of the reinforcing effects of cocaine and other addictive drugs. Using non-drug stimuli, the nucleus accumbens has also been shown to play a critical role in learning associated with reinforcement.

Behavioral research with animal models has implicated increased dopamine transmission in the NAc with behavioral responses to rewards. The exact relationship of mesoaccumbens dopamine function to the action of a reward as an incentive or as a reinforcement has been an area of controversy. The implicit assumption to the general view of dopamine transmission in the NAc is that dopamine transmission is a central correlate of the reinforcing actions of rewards. It is important to note that incentive-based reward has to do with expectancies and conditioned memories that alter future behavior or lead to adaptations of behavior. Craving in humans is a form of learned expectancy, while experiences such as cocaine-induced rush represent an acutely reinforcing effect.

Prior to the research described above, the "brain reward" circuitry was never observed in humans, nor proven to be involved with the rewarding effects of drugs such as cocaine. The research described herein allowed the localization of brain reward circuitry in the human in association with both reinforcement-based reward and incentive-based reward. Regarding incentive-based reward, this work demonstrated that a distinct pattern of brain activation is exhibited in humans during periods of craving induced by the psychostimulant cocaine. Using fMRI, which measures blood flow oxygenation changes associated with changes in neuronal activity, these studies showed that psychostimulant-induced craving (e.g., cocaine-induced craving) is correlated with early, but sustained signal maxima in the nucleus accumbens and the amygdala. This observation contrasted with the observation that fMRI activation in the basal forebrain and VT was correlated with rush. Together, these observations in humans represent the first time that circuitry found active in animals during reinforcement reward and during incentive reward has been found to function in a similar manner in humans.

The data described herein show homology between animal and human reward circuitry, it is also intriguing that the psychostimulant cocaine produces its rewarding effects in animals and humans via the same mechanism. Namely, reinforcement reward in animals depends on the change in synaptic dopamine levels in the mesoaccumbens circuit produced by cocaine-like drugs via blockade of the dopamine reuptake transporter (DAT). This change in synaptic dopamine levels leads to greater receptor occupancy at post-synaptic dopamine receptors. In both animals and humans, the acutely reinforcing effects of psychostimulant drugs can produce a pattern of repeated self-administration.

A third domain involved with brain reward and stimulant-induced euphoria in which animals and humans are similar is that of the distribution of dopamine receptor subtypes. In particular, the D1 receptor has been found in significant amounts in the nucleus accumbens and the amygdala of humans.

In animals, it has been shown that drugs that are D1 antagonists produce significant alterations of drug-related expectancies. Specifically, they are potent inhibitors of stimulant cues, alter expectancies for conditioned preferences, and can inhibit the reinforcing effects of psychostimulants such as cocaine. In one study, the alteration of expectancies for conditioned preferences in rodents was strongly associated with D1 antagonist effects in the nucleus accumbens. Accordingly, one treatment of cocaine addiction, in accordance with the invention, involves D1-antagonists, which alter function in the nucleus accumbens and/or amygdala reducing reinforcement reward, and Ĉ distribution of D1 receptors, D1-antagonists can be used to reduce expectancies in general (experienced as cue-induced or cocaine-induced craving in the human), and D1-agonists can be used to reduce cocaine-primed expectancies in humans and therefore be an effective form of treatment in humans. These methods of treatment are now possible because of the research described above, showing (a) that humans have the same extended neural network of reward circuitry as animals, and (b) that this circuitry performs both reinforcement reward and incentive reward function (e.g., for craving).

Experimental Procedures Used for Human Studies

A detailed description of the experimental procedures utilized in the above study follows.

Subjects

Of the 17 subjects who completed the experimental protocol, 13 were men and 4 were women [mean age= 34.5±4.6 years; education=12.2±1.6 years; weight= 79.6±17.8 kg; Addiction Severity Index (McLellan et al., 1980, Journal Of Nervous and Mental Disorders 168:26–33) Composite Score (0 to 1.00) on the Drug dimension= 0.18±0.13, and on the Alcohol dimension=0.27±0.25; Hamilton Anxiety Scale (0 to 54) 2.94±2.08; Hamilton Depression Scale (0 to 52) 7.53±5.66]. All subjects were right-handed. Except for cocaine addiction, they were medically and neurologically normal by physical exam, review of systems, blood work including electrolytes, liver function tests, cell blood count, and toxicology. No subject had a history of head trauma with loss of consciousness, or had any family history of sudden cardiac death or cardiac disease. All subjects tested negative for human immunodeficiency virus (HIV). Women were not pregnant by HCG testing, and were scanned at the midfollicular phase of their menstrual cycle. All subjects fulfilled criteria for cocaine dependence, with or without comorbid alcohol or marihuana abuse, by Mini-Structured Clinical Interview for DSM-IV (SCID) (American Psychiatric Association, 1994, Washington, D.C.: American Psychiatric Assoc. 4th ed. rev.). The subjects were selected to be heavy, long-term cocaine users (mean=7.8±6.0 years; days of cocaine use in 30 days prior to experiment=16.2±8.2 days). The monetary expenditure for cocaine was $397.0±318.0 over the week prior to the experiment. No subjects were seeking or receiving treatment for substance abuse at the time of the study. To be accepted into the imaging protocol, during screening, subjects had to have one positive urinalysis to confirm recent cocaine use, but had to be abstinent from cocaine and alcohol for at least 18 hours before the infusion. Approximately 18 hours before each imaging session, subjects underwent a screening IV test-dose of 0.2 mg/kg in the Massachusetts General Hospital (MGH) Mallinckrodt General Clinical Research Center (GCRC) under the supervision of a cardiologist and psychiatrist, to ascertain cardiac and neurological tolerance of the experimental procedures. They were subsequently monitored in the GCRC until the time of scanning. All subjects gave informed consent to participate in these procedures following the rules of the Subcommittee on Human Studies at MGH.

Experimental Design

Subjects were admitted to the MGH GCRC for the screening procedures; those meeting all criteria were boarded overnight on the unit in preparation for imaging the following day. The following morning the subject had bilateral intravenous catheters placed (right forearm for cocaine or saline infusion, left forearm for serial venous blood sampling for quantitative cocaine levels). Scanning was performed between 11AM and 3PM during which the subject was in the scanner for two periods of time each lasting from 45 to 90 minutes. During each scanning period, one infusion was given, either cocaine (0.6 mg/kg, maximum dose 40 mg) or saline (both in a volume of 10 cc given over 30 seconds IV) in a randomized, double blind order. Five different scans were performed during each period. The infusion itself was made 5 minutes into an 18 minute long blood oxygen level dependent (BOLD) scan. The BOLD infusion scan was bracketed by flow-sensitive alternating inversion recovery (FAIR) and visual stimulation BOLD scans (the data from these scans were used to delineate the global vs. regional signal changes from cocaine). The time interval between functional scans within a period was kept to a minimum. The entire sequence of 5 functional scans was completed within 45–60 minutes. The subject was removed from the scanner for a 15–30 minute rest and then was returned to magnet and the sequence was repeated for the second infusion. A minimum of two hours had to pass between each double-blind infusion.

Subject Instructions

For the pre-experiment test-infusion with 0.2 mg/kg cocaine on the night before scanning, subjects were informed they would receive a small dose of intravenous cocaine in the presence of a cardiologist and a psychiatrist to screen for medical side-effects from intravenous cocaine, and to train them in making behavioral ratings of their experience.

For experiments performed in the magnet, subjects were informed they would receive two infusions to which both they and the experimenters were blind. Infusions could either be saline or 0.6 mg/kg of cocaine in saline; the experience of one infusion did not imply what would be the identity of the other. Subjects were further asked to continue behavioral ratings throughout the FAIR and BOLD infusion scans (~40 minutes in total), and to remain as motionless as possible to minimize fMRI movement artifacts.

Plasma/Urine Monitoring

Sequential 4 ml venous blood samples were collected immediately before and at 1, 3, 5, 10, 15, 30, 60, 90 and 120 minutes following each infusion. The 120 minute sample for the first infusion was also the pre-infusion sample for the second infusion.

Physiological Monitoring

Physiologic monitoring was conducted using an In Vivo OmniTrak 3100 patient monitoring system (Orlando, Fla.) modified to permit on-line computer acquisition of physiologic measurements. Each subject was fitted with chest leads to record the electrocardiogram (ECG) and to measure heart rate (HR), a nasal cannula to measure respiratory rate and end-expiratory carbon dioxide ($ETCO_2$), and a blood pressure cuff to measure non-invasively systemic mean blood pressure (MBP). The temporal resolution of the system for sampling blood pressure was once every two minutes. The In Vivo system sampled and displayed updated values for each of the other parameters once per second, except for the ECG trace which was digitized at a rate of 100 Hz.

The measured physiologic parameters were ported to a Macintosh Power PC 7100 running a custom National Instruments Lab View data acquisition program. This program allowed the simultaneous acquisition of 1) the digitized analog ECG trace signal acquired using a National Instruments MIO 16L board, 2) the GE scanner J8 trigger pulse which indicated when the gradient coils of the magnet were firing and 3) serial port read of ASCII characters reporting physiologic measures from the In Vivo system.

Precautions taken to ensure safe conduct of the study included use of ACLS trained personnel, frequent running of mock codes with clocked performance of tasks and strict definition of individual tasks, and presence of a cardiologist at the time of all infusions whose sole responsibility was to monitor subject safety. Before and after completion of both infusions, subjects underwent a 12-lead ECG to determine the absence of any interval change from the experiments. Because of magnetohydrodynamic effects on the ECG tracing, a baseline rhythm strip was obtained prior to each drug infusion and all subsequent tracings were compared to that one.

Behavioral Monitoring

For both infusions, analog scales for behavioral response were projected via the Lab View program and a back projection television system (Sharp Liquid Crystal, RU2000) outside the Faraday shield of the scanner. These projected stimuli were then focused via a biconvex lens (Buhl Optical) inside the Faraday shield onto a rear-projection screen which was viewed through an overhead mirror in the magnet bore. For both infusions, subjects viewed images prior to actual experimentation so that images could be focused and centered in each subject's visual field.

During FAIR and BOLD infusion scans, behavioral measures of rush, high, low, and craving were obtained in a continuous sequence each minute. Thus, over each 15 second epoch, one rating scale would be projected for the subject's response. Given four scales, it took one minute to cycle through the complete set of scales. Timing of scan initiation, infusion onset and offset, and scan completion were linked with ongoing behavioral reports to allow subsequent correlational analysis between behavioral ratings and fMRI acquisitions. Behavioral responses were acquired with a four-button button-press which had been adapted to the magnet environment by construction with non-magnetic components and filtering of its output at the Faraday shield.

To obtain meaningful behavioral ratings during scanning, subjects were trained beforehand. The day before scanning, subjects were interviewed in depth by one of two board-certified psychiatrists to fully describe their experience of cocaine intake. These descriptions were then categorized by the psychiatrist and subject into four components: the rush, high, low, and craving which were to be rated on an integer scale of 0 (none) to 3 (maximum). The individualized conventions for description of subjective responses were then tested, during the unblinded pre-infusion with 0.2 mg/kg cocaine, on a portable computer with a program simulating that used in the MRI.

Of the four behavioral measures, only craving was defined operationally in terms of the action the individual wanted to engage in (to get more cocaine). The other three behavioral measures, rush, high, and low, were defined in terms of subjective feelings which were not necessarily associated with a behavioral output, or associated with the planning and implementation of physical activity. Thus, by definition, only craving was defined as a motivational state. In general, rush experiences involved physical sensations of elevated heart rate and sweating, along with internal feelings variously characterized as 'speeding' sensations and sensations of 'being out-of-control'. In contrast, the high experience was generally associated with feelings of self-confidence, well-being, and sociability. The low experience encompassed all negative subjective feelings potentially associated with cocaine use such as anxiety, paranoia, dysphoria, or anhedonia; the majority of subjects in this study discussed the low in terms of dysphoric affect distinct from a diminishment in the high experience.

Imaging

Scanning was performed with a quadrature head-coil and a 1.5 T MR scanner (General Electric) modified for echo-planar imaging (Advanced NMR). Imaging involved the following protocol. First, a sagittal localizer scan [conventional T1-weighted spoiled gradient refocused gradient echo (SPGR) sequence; through-plane resolution=2.8 mm; 60 slices] was performed to orient, for subsequent scans, 15 contiguous axial slices covering the whole brain. This scan was also used as the structural scan for Talairach transformation. Next, an automated shimming technique was used to optimize $B_0$ homogeneity (Reese et al., 1995, J. Magn. Reson. Imaging 5:739–745). This was followed by a SPGR T1-weighted flow-compensated scan (resolution=1.6 mm×1.6 mm×8 mm) scan, which was primarily obtained to aid Talairach transformation during data analysis (see Breiter et al., 1996, Arch. Gen. Psychiatry 53:595–606). The fourth scan was a T1-weighted echo planar inversion recovery sequence (TI=1200 msec, in-plane resolution=1.57 mm) for high-resolution structural images to be used in preliminary statistical maps, but not with Talairach transformed or averaged maps. Finally, BOLD imaging was performed using an asymmetric spin echo $T2^*$-weighted sequence (TR=8000, TE=50, 180 refocusing pulse offset by −25 ms; FOV=40×20 cm; in-plane resolution=3.125 mm; through-plane resolution=8 mm; 15 contiguous axial slices covering the whole brain) to measure 'activation' (local changes in blood flow and oxygenation) (Kwong et al., 1992, Proc. Natl. Acad. Sci. 89:5675–5679; Ogawa et al., 1992, Proc. Natl. Acad. Sci. 89:5957–5955; Bandettini et al., 1992, Magn. Reson. Med. 25:390–397). Images were acquired interleaved for 136 time points for each infusion.

Data Analysis

Plasma/Urine Levels: Cocaine quantitative assays were performed by the MGH Clinical Chemistry Laboratory using a liquid chromatography with photodiode array detection method they developed (Puopolo et al., 1992, Clin. Chem. 38:1838–1842), with minor modifications (flow rate increased from 2.0 to 2.6 ml/minute and LCPCN column length increased from 150 to 250 mm). Intra-assay imprecision at 100, 20, and 10 mg/L for cocaine is 5.1%, 5.7% and 6.6% respectively.

Physiological Data: The data analysis and graphing program IGOR (WaveMetrics, Inc.) was used to analyze the data. Data were first analyzed by a 2 way ANOVA with drug treatment (saline, cocaine) and time of measurement as factors. When significant F values were obtained for one of the physiologic measures, individual time points were compared by post-hoc t-tests to determine if (and at what times) the change from baseline was significant. The Bonferroni correction for multiple comparisons was used; the criteria for significance at the 0.05 level was p<0.007.

Behavioral Data: The integer output for each behavioral rating was segregated by category of rush, high, low, and craving. For the group data in FIG. 2, the 18 measures for each behavioral category obtained during the 18 minute BOLD infusion scan were averaged for the 9 subjects with both interpretable behavioral data and fMRI data. This averaged data was then utilized in the correlational analysis of the cocaine fMRI data.

BOLD Data for Initial fMRI Experiments, and for Test/Retest Experiments:

Motion correction: To reduce head motion, each subject was positioned using a bitebar, and echo-planar data was motion corrected using an algorithm (Jiang et al., 1995, Hun. Brain Mapp. 3:1–12) adapted from Woods et al (1992), and described elsewhere (Breiter et al., 1996, Arch. Gen. Psychiatry 53:595–606). Motion correction of the BOLD saline infusion data revealed an average maximal displacement of 1.8±2.3 mm resulting in a mean correction per time-point of 0.6±0.5 mm. For the cocaine infusion data, there was an average maximal displacement of 1.1±0.7 mm resulting in a mean correction per time-point of 0.6±0.4 mm. After motion correction, time-series data were inspected to assure that no data set evidenced residual motion in the form of cortical rim or ventricular artifacts >1 voxel. There was no statistically significant difference in maximal displacement between paired groups of saline vs. cocaine infusions (p<0.4).

Talairach transformation: Each individual's set of infusion related functional images, along with the associated conventional structural scans, were transformed into Talairach space (Talairach et al., 1988, New York: Thieme Medical Publishers; Breiter et al., 1996, Arch. Gen. Psychiatry 53:595–606; Breiter et al., 1996, Neuron 17:875–887) and resliced in the coronal orientation over 57 slices with isotropic voxel dimensions (x,y,z=3.125 mm). Because of possible movement between acquisitions of structural and functional scans, functional data were further fit to the structural scan by translation of exterior contours. For the cocaine and saline infusions, 2 subjects evidenced movement between structural and functional scans of >2 voxels in magnitude, and, therefore, were discarded from further analysis.

Normalization, Averaging & Concatenation: For cocaine and saline infusions, Talairach-transformed functional data were intensity scaled (i.e., normalized relative to a standard pre-infusion epoch) so that all mean baseline raw magnetic resonance signals were equal. Talairach-transformed structural and functional data were then averaged by run across the 10 subjects with interpretable cocaine infusion data, and the 10 subjects with interpretable saline infusion data; similar averaging of Talairach-transformed structural and functional data was performed for the four subjects used in the test/retest analysis (Breiter et al., [Abst] 1995, Proc. Soc. Magn. Reson./Euro. Soc. Magn. Reson. Med. Biol. Joint Meeting 3:1348; Breiter et al., [Abst] 1995, Proc. Soc. Neuroscience 3:1988; Breiter et al., 1996, Arch. Gen. Psychiatry 53:595–606; Breiter et al., 1996, Neuron 17:875–887).

Voxel-by-voxel statistical mapping: Unsmoothed Kolmogorov-Smirnov (KS) statistical images were constructed (Breiter et al., 1996, Arch. Gen. Psychiatry 53:595–606; Breiter et al., 1996, Neuron 17:875–887) from these averaged data sets comparing baseline (N=38 time points) and post-infusion (N=98 time points) epochs. Drift correction (i.e., removal of a first order linear function) was incorporated in the statistical calculation, but not for the signal intensity time courses shown. Subsequently, clusters of activation were determined on data which was smoothed by a 0.7 pixel gaussian filter (~Hamming filter in the spatial domain). To guide the determination of activation clusters, smoothed data sets were subjected to a cluster-growing algorithm (Jiang et al., [Abst] 1996, Acad. Press 3(3):S67; Bush et al., [Abst] 1996, Acad. Press 3(3):S55), and activation clusters listed which met a corrected p-value threshold. The cluster growing algorithm was set to select activations with maximum p-values below $p<10^{-5}$, and to separate activations with pixels of $p<10^{-4}$ between them. All activation clusters were then evaluated on the unsmoothed data to ascertain that they met cluster constraints, did not overlap areas of susceptibility, had time courses consistent with the experimental paradigm, and could be anatomically localized (see below for details). The correction for multiple comparisons of this data, in order to maintain an overall <0.05, was the Bonferroni correction for all gray matter voxels sampled in the brain, or $p<7.1\times10^{-6}$ (Breiter et al., 1996, Neuron 17:875–887). To be tabulated, activations had to meet cluster constraints on the unsmoothed KS statistical maps as follows: (a) for subcortical gray matter, three contiguous voxels with one voxel at $p<7.1\times10^{-6}$, and two voxels at $p<10^{-5}$; and (b) for cortical activations, five contiguous voxels with one voxel at $p<7.1\times10^{-6}$, and four voxels at $p<10^{-5}$. The effect of such cluster constraints on statistical significance has been discussed previously (Breiter et al., 1996, Arch. Gen. Psychiatry 53:595–606).

The time-course of signal change was evaluated for each putative activation identified on statistical maps of averaged data by the cluster-growing algorithm. These signal intensity versus time curves were assessed to ascertain that activation did not precede infusion onset. All activations had to meet these two criteria, along with anatomical constraints that the Talairach coordinate of their maximum voxel (i.e., the voxel with the lowest p-value) was in the brain as assessed by the Talairach atlas (Talairach et al., 1988, New York: Thieme Medical Publishers), and that the activation, when thresholded at $p<10^{-5}$, did not extend outside the brain when superimposed over the Talairach-transformed structural images.

Neuroanatomical Analysis: A combined approach to anatomic localization of functional data was used. The group average data (GAD) was mapped using an approach focused on Talairach coordinates. In addition, the individual data (ID) were mapped using a region of interest based approach, focused on the limbic and paralimbic areas.

Anatomic Localization of GAD: Statistical maps of group averaged data were superimposed over high-resolution conventional $T_1$-weighted images which had been transformed into the Talairach domain and averaged. Primary anatomic localization of activation foci was performed by inspection of these coronally resliced T1-weighted scans and via the Talairach coordinates of the maximum voxel from each activation cluster (see section on determination of activation clusters). Subcortical localization of activations followed the region of interest conventions described below. All activations were checked against the functional image data to ascertain that they did not overlap areas of susceptibility artifact. Such overlap was determined by whether or not a voxel's signal intensity during the baseline was less than the average voxel in its slice by 50% of the difference between the average voxel signal intensity in the slice and the average voxel signal intensity outside of the slice.

Anatomic Localization of ID: To assess the degree to which subcortical activations seen in the group represent common activations across the population, as opposed to the effect of strong activations in a few subjects, each individuals Talairach transformed T1 high resolution scan was inspected and regions of interest (ROIs) defined. Visual inspection of the superimposed KS statistical maps, thresholded at a liberal statistical threshold (KS, p<0.001), was then performed to determine if activation was present in each of the anatomic structures discussed below. These results were tabulated as a ratio of individuals showing lateralized activation in that structure to the total number of subjects evaluated (N=10). As the predictions involved only subcortical structures, the individual analysis also focused on noncortical regions, with the exception of medial paralimbic and intrasylvian cortices.

The methods used for definition of the subcortical ROIs followed the conventions of the MGH Center for Morphometric Analysis. These ROIs were defined by use of specific anatomic landmarks identified by direct visualization of each individual Talairach transformed T1 anatomic scan. These coronal scans had voxel dimensions of x,y,z=3.125 mm, a matrix of 49×37×57, and were viewed on the computer monitor with a size of 38 mm×31 mm size. Key landmarks necessary for anatomic localization included: the anterior commissure (AC), posterior commissure (PC), lateral geniculate nucleus (LGN), mammillary body (MB), substantia nigra (SN), anterior and posterior extents of amygdala, anterior and posterior extents of hippocampus, posterior extent of pulvinar, collateral sulcus and splenium of corpus callosum.

Sixteen ROIs were defined to encompass the following structures: the caudate nucleus (Cau), the nucleus accumbens and subcallosal cortex (NAc/SCC), the putamen (Put), the pallidum (GP), the amygdala (Amy), the anterior and posterior insula (aINS and pINS), the anterior and posterior hippocampus (aHIP and pHIP), the parahippocampal gyrus (Parahip), the precommissural and postcommissural cingulate gyrus (aCG and pCG), the basal forebrain (BF), the precommissural and postcommissural thalamus (aThal and pThal), the lateral geniculate nucleus (LGN), and the ventral tegmentum (VT: including SN and surrounding region). Definitions for each of these ROIs were as follows: Cau extents reached from the anterior tip of its head to the part of its body corresponding at the coronal level of the LGN. NAc/SCC was identified at the inferior junction between the head of Cau and the Put. It was delimited superiorly by a line connecting the inferior corner of the lateral ventricle and the inferior most point of the internal capsule abutting NAc/SCC and laterally by a vertical line passing from the latter point. Put, GP, VT, LGN, and Amy were directly visualized, and the posterior extent of Amy was at the identical coronal plane as the anterior tip of aHip. The posterior extent of the aHip was the coronal plane in front of the PC; the PC plane was the anterior border of pHip. The posterior border of the pHip was identified by direct visualization. Parahip was limited superiorly by the hippocarnpus or the amygdala and inferiorly by the collateral sulcus. By convention, Parahip activation behind the posterior end of the hippocampus was not considered. The insula was directly identified on the coronal plane throughout its anteroposterior extent; its anterior portion (aINS) continued to the coronal plane before the AC while its posterior extent (pINS) included the coronal plane with the AC. The precommissural cingulate (aCG) extended from the paracingulate sulcus anteriorly to the coronal plane anterior to the posterior commissure. Its sperior border was determined by the paracingulate sulcus through the coronal slice containing the AC and, behind this plane, the cingulate sulcus. Its inferior border was defined by the paracingulate sulcus (curving portion) anteriorly, and the callosal sulcus posteriorly. The postcommissural cingulate (pCG) extended from the coronal plane of the PC anteriorly, to the subparietal sulcus posteriorly. Its superior border was defined by the cingulate sulcus and the subparietal sulcus, whereas, its inferior border was the anterior portion of the calcarine sulcus (Damasio, 1995, Oxford U. Press; Caviness et al., 1996, J. Cog. Neurosci. 8:566–587). BsFor region extended anterioposteriorly from the NAc level to the SN coronal section, and medially to the hypothalamus (which extended anteroposteriorly from AC to include posteriorly the MB, having a vertical line at the level of the optic tract or the lateral most extent of the optic chiasm of the internal capsule as its lateral border and the interhemispheric midline as its medial border). The thalamus was divided anteroposteriorly in two sectors. The aThal extended from the anterior tip of the thalamus to the coronal plane anterior to the posterior commissure, and pThal extended posterior to the PC, including the PC coronal section. The thalamic ROIs were defined inferiorly by the hypothalamic fissure.

Correlational Analysis of BOLD Data from the fMRI Experiments:

A multiple correlational analysis was performed between group-averaged behavioral data (N=9), and group-averaged fMRI data (N=10). In one subject, the behavioral data was not time-locked to the scanner due to computer malfunction, thus these data were not used in the group-average of behavioral data. The multiple correlation technique involved (a) cross-correlation of the group average behavioral ratings for rush and craving with the group average fMRI data to generate correlation co-efficient (R-value) maps, and (b) transformation of the R-value maps via the Fischer transform into p-value maps. To be tabulated, an activation had to have 5 contiguous voxels with R>0.70 for each voxel. For 136 time points, an R>0.70 corresponds to a $p<10^{-20}$. Because 10 subjects were averaged, this R>0.70 corresponds to an R>0.22 in the individual. The resultant maps illustrated the brain regions whose signal change resembled the time course of rating change for each category of subjective rating.

Comparison of BOLD Data from Test Experiments with Retest Experiments:

For the subgroups of subjects which had interpretable repeat cocaine infusion scan data (N=4) and those with interpretable repeat saline infusion scan data (N=4), data analysis involving Talairach transformation, signal normalization, averaging, and statistical mapping followed the procedures described above. Also, as above, activations were determined using the same cluster-growing algorithm; activations were interrogated regarding proximity to susceptibility, relationship to experimental paradigm, and anatomy in similar manner. Activations were tabulated with the number of unsmoothed voxels in each activation cluster which met the criteria of $p<10^{-6}$. Similarity of activation between test and retest conditions was determined by the proximity of the maximum voxels (i.e., with reference to p-value threshold) for each activation, and by overlap between the set of voxels in each cluster which met the threshold of $p<10^{-6}$ (note: the Bonferroni threshold for multiple comparisons is $p<7.1\times10^{-6}$). To be considered "similar" activations, they had to have their maximum voxels within 1.5 cm of each other, or have at least one overlapping voxel at the strict $p<10^{-6}$ threshold.

Example II

Animal Studies

In the following example, a drug-naive rat model was used to identify the anatomical and temporal pattern of brain activation induced by cocaine. Chronic drug use animal models can be used in a similar fashion. As in the human studies described above, BOLD fMRI in this drug-naive rat model was used to map cocaine-induced brain activation. In addition, cocaine-induced activation of cerebral blood flow (CBF) was mapped using laser Doppler-flowmetry, and cocaine-induced activation of cerebral blood volume (CBV) was mapped using MRI after injection of the contrast agent monocrystalline iron oxide nanocolloid (MION). A dose-dependent, region-specific activation of cortical and subcortical structures was detected, and was particularly evident in regions with significant dopaminergic innervation. In addition, these data show a close temporal coupling of BOLD contrast CBF and CBV in frontal cortex during activation. Similarly, both the dose response and the anatomic extent of cortical activation determined with BOLD signal agreed well with the regional specificity of increased CBF and CBV.

Experimental Procedures Used for Animal Studies

A detailed description of the experimental procedures utilized in the animal studies follows.

Animal Preparation

All procedures were carried out in accordance with NIH guidelines. Male Harlan Sprague-Dawley rats (225–300 gm) were anesthetized briefly with 1.5% halothane in oxygen for insertion of left femoral arterial and venous cannulae and placement of tracheostomy for mechanical ventilation (using a 16 gauge intravenous catheter, Inste-W, Becton Dickinson, Sandy, Utah). All wounds were infiltrated with 1% lidocaine before incision. Following surgery, the inspired halothane concentration was reduced to 0.7% and rats were paralyzed with 2 mg/kg intravenous pancuronium, followed by a continuous intravenous infusion of pancuronium at 2 mg/kg/hr. Pancuronium was dissolved in normal saline administered at 5 ml/kg/hr. Rats were mechanically ventilated (in a small animal volume controlled ventilator, Harvard Apparatus, Inc., South Natick, Mass.) with a 80/20 air/oxygen mixture, an inspiratory to expiratory ratio of 1:1, and an initial tidal volume of 3.0 ml at a rate of 40 breaths per minute. Ventilation parameters were adjusted to maintain normal arterial blood gases (pH=7.40±0.01, $PaCO_2$=40±2, $PaO_2$=145±10). Arterial blood samples (150 $\mu$l) withdrawn from cannula were analyzed for arterial partial pressures of oxygen, carbon dioxide, and pH (Ciba-Coming Model 1304) before administration of drugs, and at the end of each experiment before sacrifice, to ensure animal stability. Arterial blood pressure and rectal temperature were monitored throughout the experiment. Only animals that exhibited stable physiological parameters were induced for analysis. Rats torsos were wrapped in two heating blankets (Gaymar, Orchid Park, N.Y.) circulating warm water to maintain core temperature at 37–38° C. To minimize MRI motion artifact, rats were placed into a custom plastic cradle attached to a head frame machined from delrin plastic (David Kopf Instruments, Fremont, Calif.); heads were fixed with plastic screws inserted into the ear canals and a bar inserted under the front incisors. Rat heads were shaved and covered with gel toothpaste to reduce magnetic susceptibility artifacts arising from air-tissue interfaces; ear canals and oropharynx were also filled with toothpaste. A surface coil was secured over the dorsal surface of the head before positioning the animal in the magnet center. Cocaine (RBI, Natick, Mass.), SCH-23390 (RBI, Natick, Mass.), and cocaine methiodide (NIDA, Bethesda, Md.) were dissolved in normal saline and administered in a 0.5 ml volume at a rate of 1 ml/min via the femoral vein. Sixty minutes passed before injections of cocaine were repeated.

Magnetic Resonance Imaging and Analysis

A 30 mm transmit and receive linear radio frequency surface coil was used in all studies for brain water excitation and detection. Prior to functional imaging, a multislice set of high resolution conventional $T_2$-weighted coronal rat brain images was used to localize the anterior commissure. Functional MRI studies employed multislice gradient echo planar imaging of 8–16 contiguous coronal rat brain slices of 1 mm thickness with the first slice approximately 2 mm rostral to the anterior commissure; typical voxel resolution was 0.6 $mm^3$ at 1 mm slice thickness. Images were acquired with gradient echo times of 25 ms and repetition time of 5 sec; 2 averages were acquired for each time point (10 sec temporal resolution).

BOLD fMRI studies were conducted at a magnetic field strength of 4.7 Tesla (Omega Spectrometer, General Electric NMR Instruments, Fremont, Calif.). To remove echo time (Te) dependence and create a quantity that approximately reflects deoxyhemoglobin concentration, BOLD signal (S) was converted to transverse relaxation rate ($\Delta R_2^*$ as $\Delta R_2^*$=-ln$\{S(t)/S(0)\}/T_E$ (Ogawa, et al., 1993, Magn. Reson. Med. 29:205–210; Ogawa, et al., 1993, 12th Annual Scientific Meeting SMRM, pp. 618; and Ogawa, et al., 1993, Biophys. J. 64:803–812).

All CBV-weighted fMRI studies were performed at a field strength of 2 Tesla (SISCO spectrometer, Varian Spectroscopic Instruments, Palo Alto, Calif.). To obtain MRI signal that was highly weighted by CBV, a mono-crystalline iron oxide nanocolloid (MION) was injected at an iron dose of 12 mg/kg. MION was synthesized using previously described techniques (Shen, et al., Magn. Reson. Med. 29:599–604 and Mandeville, et al., 1997, Magn. Reson. Med. 37:885–890); the biodistribution (Schaffer, et al., 1993, Magn. Reson. Imag. 11:411–417) and physicochemical properties (Shen, et al., Magn. Reson. Med. 29:599–604; Jung, et al., 1996, Int. Soc. Magn. Reson. Med., 4th Annual Meeting, pp. 1681) have been reported. The blood half life of MION is approximately 4 hours in rats (Jung, et al., 1996, Int. Soc. Magn. Reson. Med., 4th Annual Meeting, pp. 1681); brain transverse relaxation rate following injection of unlabeled MION shows no detectable change for three hours after equilibration in the blood (Mandeville, et al., 1997, Magn. Reson. Med. 37:885–890). Percent change in CBV was calculated by assuming a linear relationship between the local blood volume fraction (V) and the change in relaxation rate (calculated as described above) after MION injection as:

$$\frac{\Delta V(t)}{V(0)} = \frac{\Delta R_2^*(t)}{\Delta R_2^*(0)} - 1.$$

Using this technique, hypercapnia-induced changes in CBV compare well with similar determinations made by position emission tomography (PET) and x-ray computed tomography (Zaharchuk, et al., 1997, Magn. Reson. Med. 37: 170–175; Mandeville, et al., 1998, Magn. Reson. Med. 39:615–624; and Payen, et al., 1998, Anesthesiology 88:984992).

Region of interest (ROI) analyses were applied to the time series for both BOLD and CBV weighted images. To generate a dose response relationship, a 2.7 $mm^3$ volume of bilateral frontal cortex, approximately 2 mm anterior and 2 mm lateral to bregma, was selected from both rCBV and BOLD image sets. BOLD $R_2^*$ and relative change in CBV were calculated by comparison of the average signal during the 5 min pre-drug baseline with the signal from 1 to 11 minutes after infusion of cocaine. Similarly, in order to identify brain regions in which there was significant change in fMRI signal, each voxel in the image was subjected to a Student's group t-test to determine the statistical significance of signal change between a 5 min pre-drug baseline and 1 to 11 minutes after the drug infusion. Maps were generated for BOLD and CBV image series for both positive and negative signal change.

Laser Doppler-Flowmetry

Regional cortical blood flow was determined by LDF (Perimed, PF2B, Stockholm, Sweden) as described previously (Ayata, et al., 1996, J. Cereb. Blood Flow Metab., 16:539–541). Rats (n=8) were prepared exactly as for dynamic MR studies and positioned in a standard stereotaxic head frame. With the scalp incised and retracted, two holes (1–2 mm in diameter) were drilled through the skull 2 mm lateral to midline; one hole was 2 mm anterior to bregma overlying frontal cortex, and the other was 8 mm posterior to bregma to examine occipital cortex. The flow probe was positioned directly upon exposed dura mater in a puddle of mineral oil. The location overlying frontal cortex corresponded to the region of interest for BOLD and CBV fMRI analysis. A 12 kHz band with a sampling rate of 40 Hz was used; data were resampled at 5 Hz for analysis. All data were collected, stored, and analyzed using MacLab/8 data acquisition and analysis system (ADInstruments, Mountain View, Calif.). Arterial pressure was continuously monitored and the data stored; heart rate was calculated from arterial pressure pulses by the data acquisition software. To convert LDF signal to the percentage change in CBF following cocaine infusion, LDF signal was normalized to the 5 minute period immediately preceding the start of drug infusion; the offset of LDF signal at zero flow was set as the signal remaining after death by asphyxiation.

Results of Animal Studies

Dose Response

Figure 4A:
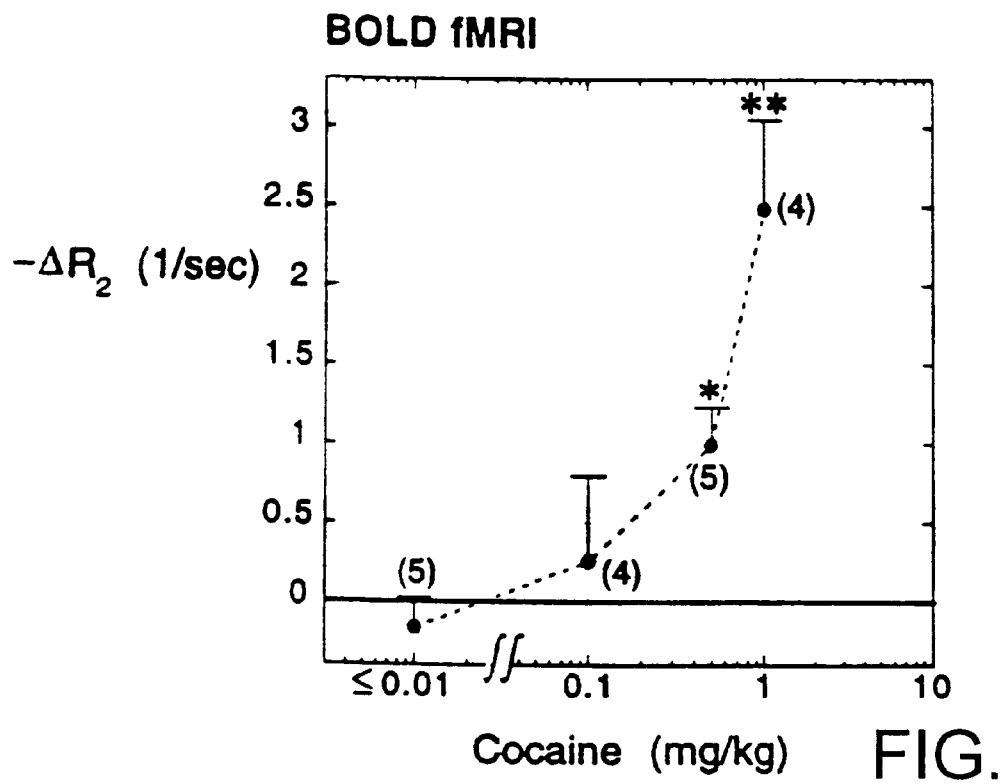
FIGS. 4A and 4B are graphs showing a dose dependent response after cocaine infusion in frontal cortex measured with (FIG. 4A) blood oxygen level dependent (BOLD) signal and (FIG. 4B) laser Doppler-flowmetry (LDF). Data are presented as MEAN±SEM for (FIG. 4A) $R_2$ detected in a 2.7 mm$^3$ bilateral volume of frontal cortex approximately 2 mm rostral to anterior commissure and 2 mm lateral to midline and (FIG. 4B) percent cerebral blood flow (CBF) measured by LDF in approximately the same region of frontal cortex as in (FIG. 4A) in a separate set of rats. The sample size is presented in parenthesis, and significant differences between pre-and post-infusion signals (as determined by paired t-test) are indicated as: *, P<0.02; **, p<0.05. Since no significant response was detected either with saline controls or cocaine doses ≦0.01 mg/kg, these values were combined.

Acute intravenous cocaine infusion increased blood oxygen level dependent (BOLD) signal in rat frontal cortex. FIG. 4A illustrates the dose dependence of the response detected in frontal cortex approximately at the level of the anterior commissure. The increase in BOLD contrast ($-R_2$) was calculated by comparing the average signal before cocaine infusion with the average signal during the period one to eleven minutes after injection of drug. Cocaine produced a significant change in BOLD signal at doses of 0.5 mg/kg ($p<0.02$) and 1.0 mg/kg ($p<0.05$) as measured with a paired t-test. A maximal $R_2$ of 2.5±0.6 sec$^{-1}$ was measured at 1 mg/kg, while little or no change in $R_2$ was seen below 0.1 mg/kg. At doses above 5 mg/kg, the response was associated with profound hypotension and cardiac arrhythmia.

Figure 4B:
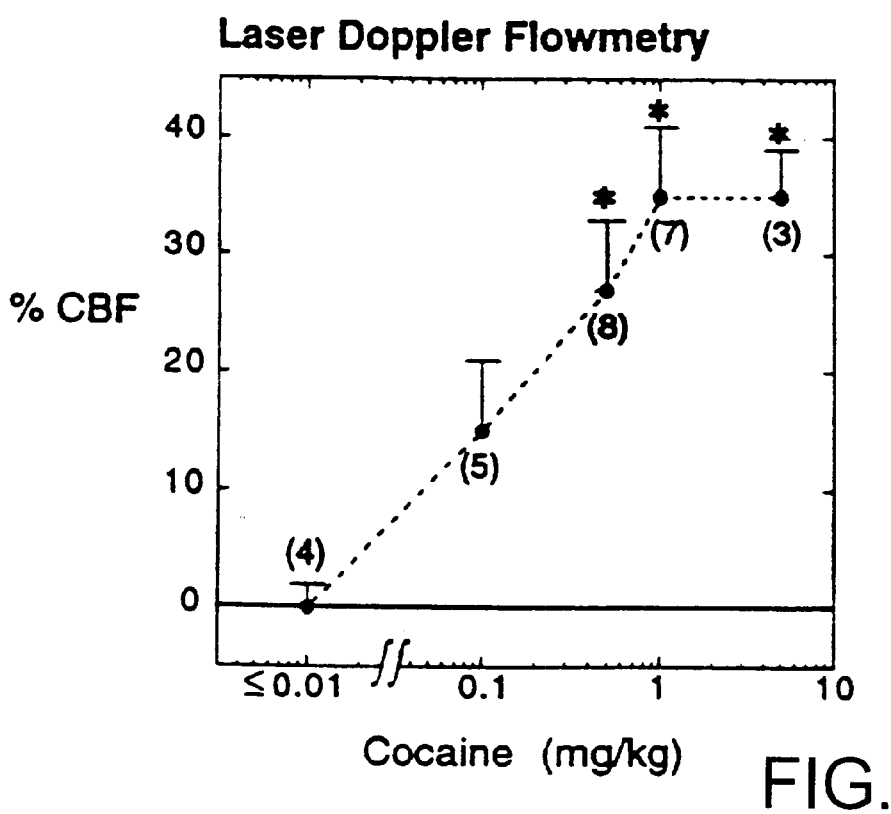

The enhanced BOLD signal was verified as corresponding to increased blood flow by measuring CBF and LDF in approximately the same region of frontal cortex as examined with BOLD fMRI. As shown in FIG. 4B, CBF response to cocaine infusion closely paralleled BOLD response. CBF increased significantly after 0.5, 1.0, and 5 mg/kg ($p<0.02$, paired t-test) with little or no change below 0.1 mg/kg. The maximum elevation of frontal cortex blood flow was 35±3 after 1 mg/kg cocaine.

Temporal Response

The CBF response as measured by LDF in frontal cortex was similar for BOLD and CBV contrast determined by dynamic MRI. Time dependent changes in CBF, CBV, and BOLD contrast induced by cocaine are shown in FIG. 5. Both cortical CBF and CBV rose sharply after drug infusion and peaked at a maximum increase of 41% and 32% over baseline, respectively, within approximately 3.5 minutes. CBF and CBV returned to baseline by 25 minutes post infusion. BOLD contrast followed a similar time course; peak $R_2$ occurred at 4 minutes and returned to baseline 20 minutes after infusion. The temporal response of BOLD contrast, CBV, and CBF did not differ significantly between 0.5 and 1.0 mg/kg cocaine.

Cocaine infusion was associated with a transient and small (5–10 mm Hg) increase in arterial blood pressure which resolved before changes in BOLD, CBF, or CBV were detected (FIG. 5B). A bolus infusion of cocaine methiodide, a positively charged quaternary cocaine derivative which does not cross the blood brain barrier (Schindler, et al, 1992, Eur. J. Pharmacol. 213:99–105 and Hemby, et al., 1994, J. Cereb. Blood Flow Metab. 9:323–328) at doses of 1, 5, 10, and 20 mg/kg produced a transient decrease in both blood pressure and heart rate, but did not produce any significant change in frontal cortex CBF (data not shown), indicating that the changes in fMRI signal observed with cocaine are a direct consequence of cocaine-induced regional alteration in brain activity and are not due to systemic effects of cocaine or a global effect on cerebral vasculature.

Regional Specificity of Response

Figure 6A:
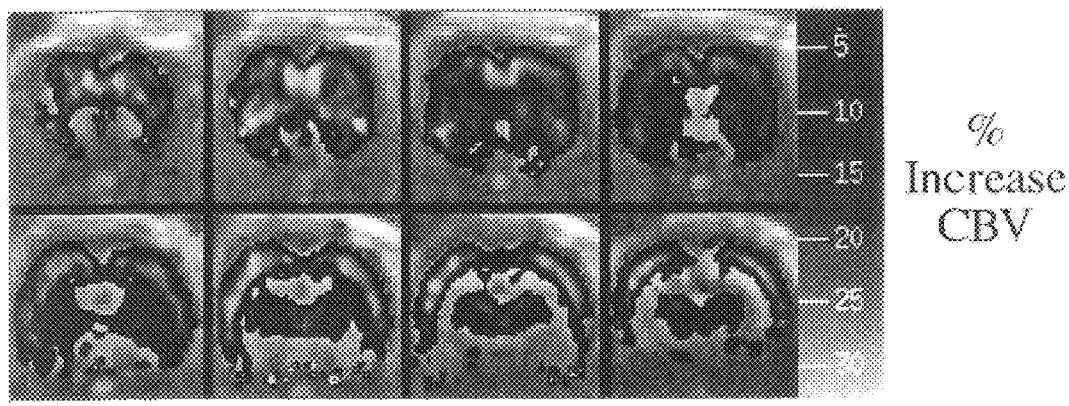
FIG. 6A is a representative map of regional CBV response in rat after infusion of 0.5 mg/kg cocaine. Data are presented for 8 consecutive 1 mm thick coronal slices; the first slice is approximately 2 mm rostral to anterior commissure. The percent increase in CBV is depicted in light shades of grey (range 2%–33%) overlying T2 weighted echo planar images.

Since CBV-weighted fMRI significantly improves functional sensitivity relative to BOLD fMRI (Mandeville, et al., 1998, Magn. Reson. Med. 39:615–624), this technique was used to map the regional activation pattern induced by cocaine infusion. A typical cocaine activation map produced using MION contrast is shown in FIG. 6. Acute cocaine infusion increased CBV in multiple regions, with the largest increase in frontal cortex. Regional variations in CBV were detected in the forebrain with gradients of rostral greater than caudal, and medial greater than lateral CBV signal identified in cortex. Activation of subcortical structures was also evident with discrete regional increases within ventral and dorsolateral striatum, nucleus accumbens, and dorsal thalamus. No significant changes in CBV were detected in cerebellum, hippocarnpus, hypothalamus, midbrain tegmentum, medulla, or pons ($p>0.05$ compared to pre-drug baseline in all regions).

Regional brain activation detected with BOLD contrast agreed closely within the region-specific increases in CBV after cocaine. The largest magnitude $R_2$ was observed in frontal neocortex; $R_2$ was smaller in lateral and occipital cortex. BOLD signal changes were seldom apparent in subcortical structures including striatum and thalamus, a result which presumably reflects the reduced sensitivity of that technique relative to CBV-weighted fMRI. No significant decrease in BOLD signal was apparent in any parenchymal region after cocaine infusion. Large increases in BOLD signal were observed in large venous structures, including sinuses (sagital, transverse and straight) and the plexus of vessels surrounding thalamus. Excluding large venous artifacts, the pattern of detectable BOLD signal changes was consistent with the regional activation pattern produced using CBV contrast.

Figure 6B:
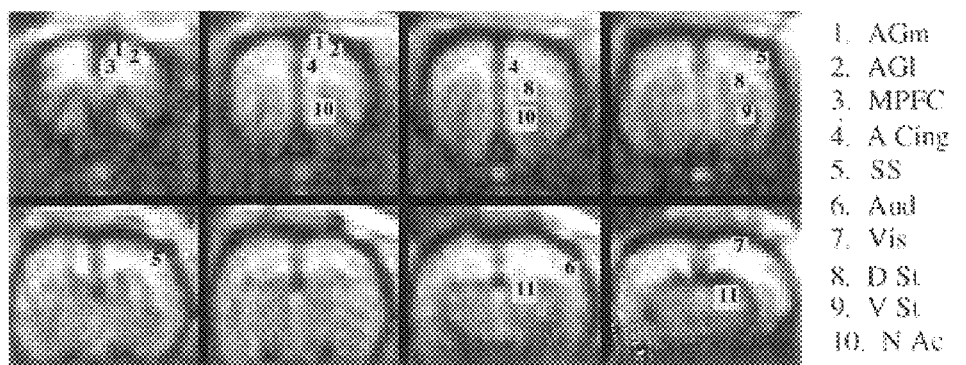
FIG. 6B is a series of T2 weighted echo planar images of slices used in FIG. 6A. The numbered overlays depict regions of interest for time course analysis: 1. AGm, agranular medial frontal cortex; 2. AGl, agranular lateral frontal cortex; 3. MPFC, medial prefrontal cortex; 4. A Cing, anterior cingulate cortex; 5. SS, somatosensory cortex; 6. Aud, auditory cortex; 7. Vis, visual cortex; 8. D ST, dorsal striatum; 9. V St, ventral striatum; 10. N Ac, nucleus accumbens; 11. D Thal, dorsal thalamus.
Figure 6C:
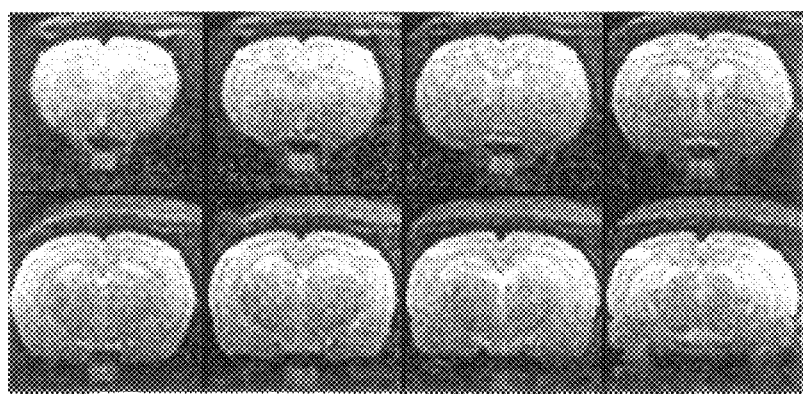
FIG. 6C is a series of high resolution conventional T2 weighted images of the same slices used in FIG. 6A.
Figure 7A:
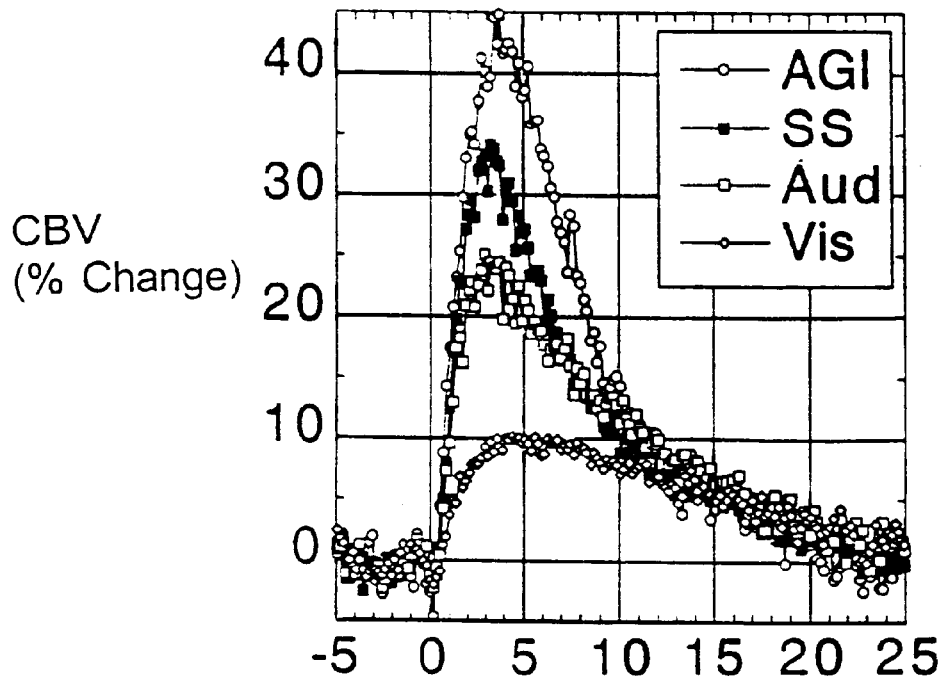
FIGS. 7A–7D are graphs showing time dependent changes in CBV within brain regions of interest after 0.5 mg/kg cocaine infusion. Regions and abbreviations are as given in the description of FIG. 6B. Cocaine was infused at Time=0 minutes. Data represent average percent changes in CBV (n=4) relative to a 5 minute baseline obtained immediately before cocaine infusion.
Figure 7B:
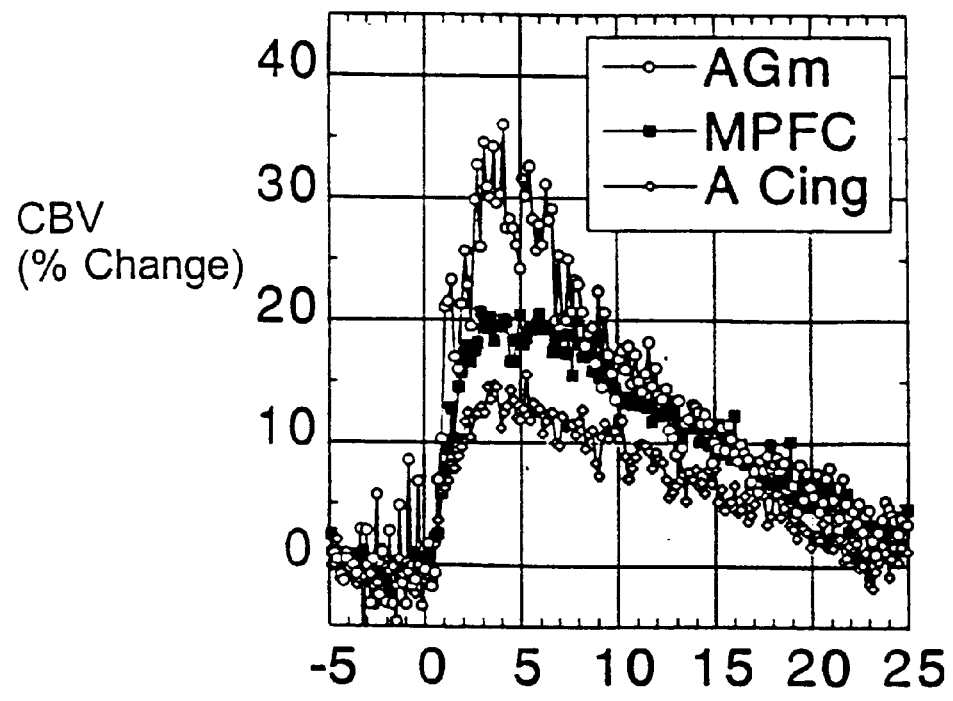
Figure 7C:
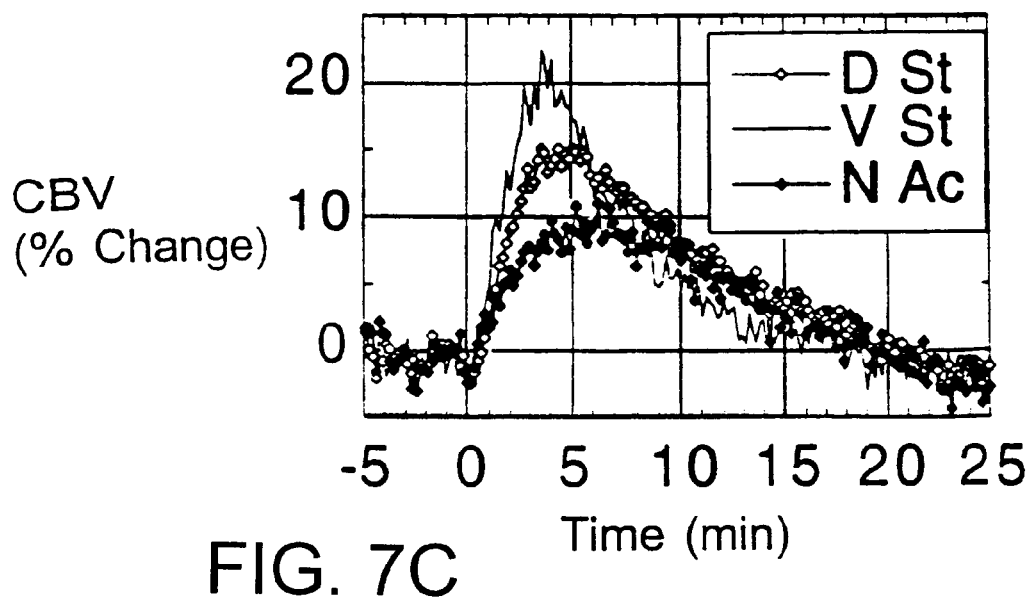
Figure 7D:
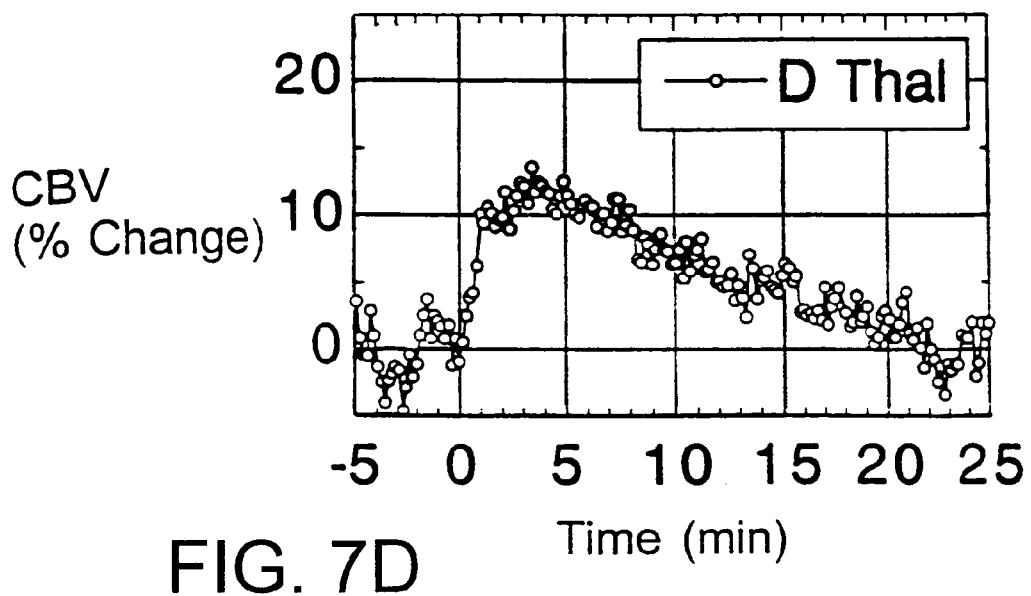

Because cocaine stimulates dopaminergic neuronal transmission within brain, the magnitude and duration of changes in CBV after 0.5 mg/kg cocaine infusion was examined in eleven brain regions including forebrain sites with rich (e.g., frontal cortex) and sparse (e.g., occipital cortex) dopamine innervation (FIG. 6B). As the CBV map indicates, cocaine infusion produced the greatest activation and frontal cortical regions (FIGS. 7A & 7B); agranular medial and agranular lateral frontal neocortex exhibited the largest increases in CBV at peak, approximately 40% and 30%, respectively. The magnitude of response was smaller in more lateral and occipital neocortical regions including somatosensory, auditory, and visual cortex. These results were consistent with BOLD and LDF data. No significant change in CBF was detected by LDF in the occipital pole even after infusion of 5 mg/kg cocaine. Similarly, when the same region of interest analysis was applied to images obtained with BOLD contrast, the magnitude of $R_2$ was less in occipital and lateral cortex when compared to frontal cortex.

The magnitude of the CBV response was significantly larger in cortical versus subcortical structures. The average response of the four subcortical regions examined (dorsal and ventral striatum, nucleus accumbens and dorsal thalamus) was only 45% as large as the five frontal and parietal cortical regions (p<0.005, group t-test). The time course, however, was similar in all cortical and subcortical regions; maximum CBV change was achieved within 3–6 minutes after initiation of cocaine infusion and returned to baseline over the succeeding 20 minutes.

D1 Receptor Mechanism

Figures 8A, 8B:
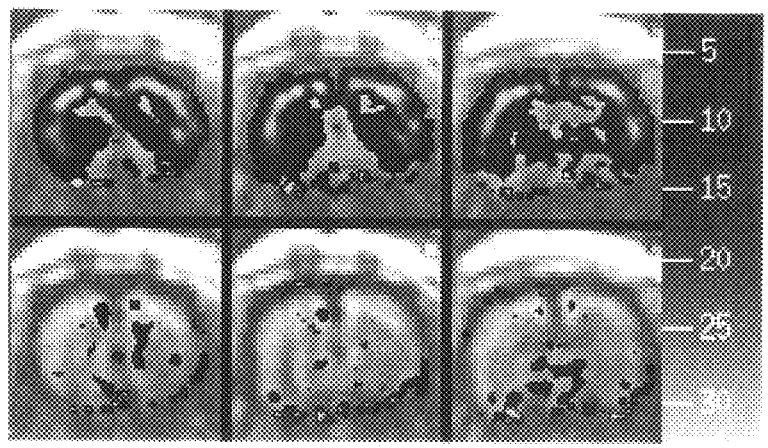
FIGS. 8A and 8B are a series of images showing that pretreatment by SCH-23390 blocked functional activation in rat brain after 0.5 mg/kg cocaine infusion. Representative regional maps of CBV increase are shown in 3 consecutive 1 mm thick coronal slices of rat brain; the first slice is approximately at the level of anterior commissure. The average percent increase in CBV is depicted in light shades of grey (range 2%–33%) overlying T2 weighted echo planar images. For FIG. 8A, the rat received no pretreatment; for FIG. 8B, the rat was pretreated with 0.1 mg/kg SCH-23390 15 minutes before cocaine infusion.

Pretreatment of rats with either 0.1 or 0.5 mg/kg SCH-23390, a selective D1 receptor antagonist, 15 minutes before infusion of 0.5 mg/kg cocaine completely blocked cocaine-induced increases in CBV (FIG. 8), although a small, transient decrease in CBV was observed in both frontal neocortex and dorsal striatum (FIG. 9). CBV reached nadir within 2 minutes post cocaine infusion with a 5% and 8% drop in frontal neocortex and striatum, respectively. Administration of SCH-23390 alone produced a small, region specific decrease in CBV in a distribution of structures similar to that in which CBV increased after infusion of cocaine without SCH-23390 pretreatment.

Results obtained using LDF in frontal cortex were consistent with the CBV-fMRI data. SCH-23390 (0.5 mg/kg) blocked cocaine-induced CBF activation in frontal cortex for all measured cocaine doses up to 5 mg/kg. Furthermore, 0.5 mg/kg cocaine infusion following pretreatment with SCH-23390 produced a small decrease in CBF of −18±3% (n=3, p<0.04, paired t-test) relative to the pre-drug baseline. These data show that cocaine-induced brain activations are mediated by the D1 receptor, suggesting that D1-like agonists and D1-like antagonists can be used to inhibit psychostimulant-induced and nicotine-induced cravings.

Summary

In sum, the various methods used in the animal studies described above show a distinct pattern of brain activation that results from the selective action of cocaine on particular cortical and subcortical targets, resulting in neural activation within specific structures of the brain. The pattern of brain activation observed with animals shows significant overlap with the pattern of brain activation observed in humans after acute cocaine administration. Pretreatment of animals with the D1 receptor antagonist SCH-23390 attenuated cocaine-induced brain activation, indicating that the D1 receptor mediates the acute action of cocaine in the brain, and supporting the conclusion that D1-like agonists and D1-like antagonists can be used to attenuate psychostimulant-induced and nicotine-induced cravings in humans.

Example III

Animal Model System

Now that the pattern of psychostimulant-induced brain activation in rodents has been shown to overlap the pattern of psychostimulant-induced brain activation in humans, rodents can be used as a model system to measure the ability of test compounds to inhibit psychostimulant-induced or nicotine-induced craving in humans. In this method, a test compound of interest is administered to a rodent prior to administration of a psychostimulant or of nicotine, and the ability of the test compound to attenuate brain activation by the psychostimulant or nicotine is measured. Attenuation of brain activation can be measured by measuring an attenuation in the level of activation obtained after administration of (a) the test compound and (b) the psychostimulant or nicotine, as compared with the level of brain activation obtained upon (a) administration of the psychostimulant or nicotine to the rodent without (b) administration of the test compound. Test compounds that cause such a relative attenuation in the level of brain activation can be used to inhibit psychostimulant-induced or nicotine-induced craving in humans.

In this method, rodents such as rats and mice are suitable. The rodent can be naive, in that it has not previously been exposed to pyschostimulants or nicotine, or an animal that was chronically using a psychostimulant or nicotine may be used. The test compound generally is administered at a dosage of 0.001 to 100 mg/kg (e.g., 0.1 to 1.0 mg/kg) of body weight of the rodent. The test compound can be formulated for administration, and administered, via any of various routes, such as intravenous, oral, intranasal, intrabronchial, and intramuscular routes, as described above for D1-like antagonists and agonists. Typically, the test compound is a D1-like agonist or antagonist, such as those described herein. The test compound can be administered to the rodent at 0 minutes to 2 days (e.g., 15 minutes to 1, 2, 4, or 8 hours) prior to administration of the psychostimulant or nicotine to the mammal. The psychostimulant (e.g., cocaine or amphetamine) or nicotine typically is administered at a dosage of 0.1 mg/kg to 10 mg/kg of body weight of the animal. Attenuation of pyschostimulant-induced or nicotine-induce brain activation (i.e., a relative decrease in the level of brain activation) can be measured using any of the art-accepted methods for measuring levels of brain activation. The above-described methods of BOLD fMRI, contrast fMRI, and laser Doppler-flowmetry can be used to measure the ability of a test compound to attenuate psychostimulant-induced or nicotine-induced brain activation and thereby inhibit psychostimulant-induced or nicotine-induced craving. Test compounds that inhibit psychostimulant-induce or nicotine-induced brain activations in this animal model can be administered to humans in a method of inhibiting craving of psychostimulants or nicotine. Typically, the test compound is administered to the human at a dosage of 0.001 to 100 mg/kg (e.g., 0.1 to 1.0 mg/kg) of body weight of the patient. The test compounds that inhibit psychostimulant-induce or nicotine-induced brain activations in rodents can be formulated for administration, and administered, to humans via any of the various routes described herein for D1-like agonists and antagonists.

Other Embodiments

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting a cocaine-induced craving in a mammal, the method comprising:

identifying the mammal as being cocaine-dependent and administering to the mammal SCH 23390 in an amount effective to inhibit craving of cocaine.

2. The method of claim 1, wherein the mammal is a compulsive cocaine user.

3. A method for inhibiting cocaine-induced craving in a mammal, the method comprising:

identifying the mammal as being cocaine-dependent; and administering to the mammal SCH 23390.

4. The method of claim 3, wherein SCH 23390 is administered at a dosage of 0.0001 to 100 mg/kg of the body weight of the mammal.

5. A method for measuring the ability of a test compound to inhibit cocaine-induced craving in a human, the method comprising:

administering the test compound to a rodent;

administering cocaine to the rodent; and measuring a modulation of the level of brain activation in the rodent subsequent to administration of (a) the test compound and (b) the cocaine, as compared with the level of brain activation obtained upon (a) administration of the cocaine to the rodent without (b) administration of the test compound, as a measure of the ability of the test compound to inhibit cocaine-induced craving in a human.

6. The method of claim 5, wherein the rodent is a rat.

7. The method of claim 5, wherein the rodent is a mouse.

8. The method of claim 5, wherein the test compound is a D1-antagonist.

9. The method of claim 8, wherein the D1-antagonist is selected from the group consisting of SCH 39166; SCH 23388; SCH 23390; A-69024; bulbocapnine; butaclamol HCl,(+)-; fluphenzanine HCl; flupenthixol 2 HCl, cis-(Z)-, fluspirilene; haloperidol; SCH-12679; SKF-83566; thioridazine HCl; thiothixine HCl; trifluoperazine 2HCl; and trifluorperidol HCl.

10. The method of claim 5, wherein the test compound is administered at a dosage of 0.0001 to 100 mg/kg of the body weight of the rodent.

11. The method of claim 5, wherein the test compound is administered 0 minutes to 2 days prior to administration of the cocaine to the rodent.

12. The method of claim 5, wherein the modulation is measured by functional magnetic resonance imaging.

13. The method of claim 12, further comprising administering a contrast agent to the rodent prior to measuring a modulation of the level of brain activation in the rodent.

14. The method of claim 13, wherein the contrast agent is a monocrystalline iron oxide nanocolloid particle or gadolinium.

15. The method of claim 5, wherein the modulation is measured by laser Doppler-flowmetry.

16. The method of claim 5, wherein the modulation of the level of brain activation is an attenuation of the level of brain activation.

17. The method of claim 3, wherein the SCH 23390 is administered intravenously.

18. The method of claim 3, wherein the SCH 23390 is administered within 0 to 168 hours of consumption of cocaine by the mammal.

19. The method of claim 3, wherein the mammal is a human.

20. The method of claim 3, wherein the mammal is a compulsive cocaine user.

* * * * *

UNITED STATES PATENT AND TRADEMARK OFFICE
CERTIFICATE OF CORRECTION

PATENT NO. : 6,517,812 B1
DATED : February 11, 2003
INVENTOR(S) : Hans C. Breiter et al.

It is certified that error appears in the above-identified patent and that said Letters Patent is hereby corrected as shown below:

Column 27,
Line 44, "Coming" should be -- Corning --.

Column 30,
Line 37, "hippocarnpus" should be -- hippocampus --.

Column 33,
Line 31, "cis" should be -- *cis* --.

Signed and Sealed this

Fourteenth Day of October, 2003

JAMES E. ROGAN
*Director of the United States Patent and Trademark Office*